United States Patent
Soni et al.

(10) Patent No.: US 11,720,647 B2
(45) Date of Patent: Aug. 8, 2023

(54) SYNTHETIC TRAINING DATA GENERATION FOR IMPROVED MACHINE LEARNING MODEL GENERALIZABILITY

(71) Applicant: GE Precision Healthcare LLC, Milwaukee, WI (US)

(72) Inventors: Ravi Soni, San Ramon, CA (US); Tao Tan, Eindhoven (NL); Gopal B. Avinash, San Ramon, CA (US); Dibyajyoti Pati, Dublin, CA (US); Hans Krupakar, San Ramon, CA (US); Venkata Ratnam Saripalli, Danville, CA (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 428 days.

(21) Appl. No.: 16/999,665

(22) Filed: Aug. 21, 2020

(65) Prior Publication Data
US 2022/0058437 A1 Feb. 24, 2022

(51) Int. Cl.
*G06F 18/214* (2023.01)
*G06N 20/00* (2019.01)
(Continued)

(52) U.S. Cl.
CPC ........ *G06F 18/2148* (2023.01); *G06F 18/214* (2023.01); *G06F 18/2163* (2023.01);
(Continued)

(58) Field of Classification Search
None
See application file for complete search history.

(56) References Cited

U.S. PATENT DOCUMENTS

| 2019/0130218 A1* | 5/2019 | Albright | G06N 3/084 |
| 2019/0340763 A1* | 11/2019 | Laserson | G06N 3/0454 |

(Continued)

FOREIGN PATENT DOCUMENTS

| CN | 110245587 A | * | 9/2019 | G06K 9/0063 |
| CN | 110909654 A | * | 3/2020 | G06K 9/00228 |

(Continued)

OTHER PUBLICATIONS

Frid-Adar et al., "Endotracheal Tube Detection and Segmentation in Chest Radiographs using Synthetic Data," arXiv:1908.07170v1 [eess IV], Aug. 20, 2019, 9 pages.
(Continued)

*Primary Examiner* — Emily C Terrell
*Assistant Examiner* — Nathan J Bloom
(74) *Attorney, Agent, or Firm* — Amin, Turocy & Watson, LLP

(57) ABSTRACT

Systems and techniques that facilitate synthetic training data generation for improved machine learning generalizability are provided. In various embodiments, an element augmentation component can generate a set of preliminary annotated training images based on an annotated source image. In various aspects, a preliminary annotated training image can be formed by inserting at least one element of interest or at least one background element into the annotated source image. In various instances, a modality augmentation component can generate a set of intermediate annotated training images based on the set of preliminary annotated training images. In various cases, an intermediate annotated training image can be formed by varying at least one modality-based characteristic of a preliminary annotated training image. In various aspects, a geometry augmentation component can generate a set of deployable annotated training images based on the set of intermediate annotated training images. In
(Continued)

various instances, a deployable annotated training image can be formed by varying at least one geometric characteristic of an intermediate annotated training image. In various embodiments, a training component can train a machine learning model on the set of deployable annotated training images.

**20 Claims, 25 Drawing Sheets
(1 of 25 Drawing Sheet(s) Filed in Color)**

(51) Int. Cl.
  *G06F 18/21* (2023.01)
  *G06N 3/08* (2023.01)
  *G06N 20/10* (2019.01)
  *G06V 10/774* (2022.01)
  *G16H 30/40* (2018.01)
  *G06T 11/00* (2006.01)

(52) U.S. Cl.
  CPC ............... *G06N 3/08* (2013.01); *G06N 20/00* (2019.01); *G06N 20/10* (2019.01); *G06T 11/00* (2013.01); *G06V 10/774* (2022.01); *G16H 30/40* (2018.01); *G06V 2201/03* (2022.01)

(56) References Cited

U.S. PATENT DOCUMENTS

| | | | |
|---|---|---|---|
| 2020/0057918 A1 | 2/2020 | Shin et al. | |
| 2020/0320347 A1* | 10/2020 | Nikolenko | G06N 20/00 |
| 2020/0364864 A1* | 11/2020 | Shanbhag | G06T 7/0012 |
| 2020/0394459 A1* | 12/2020 | Xu | G06N 3/0472 |
| 2021/0124994 A1* | 4/2021 | Bui | G06V 20/64 |
| 2021/0158137 A1* | 5/2021 | Sasao | G06F 7/24 |
| 2021/0173095 A1* | 6/2021 | Kang | G06V 10/82 |

FOREIGN PATENT DOCUMENTS

| | | | | |
|---|---|---|---|---|
| CN | 111340775 A | * | 6/2020 | G06T 7/0012 |
| CN | 111627080 A | * | 9/2020 | G06N 3/0454 |

OTHER PUBLICATIONS

Yi et al., "Automatic catheter detection in pediatric X-ray images using a scale-recurrent network and synthetic data," 1st Conference on Medical Imaging with Deep Learning, arXiv:1806.00921v1 [cs.CV], Jun. 4, 2018, 10 pages.

"Albumentations," https://github.com/albumentations-team/albumentations, last accessed Aug. 17, 2020, 14 pages.

"Imgaug," https://github.com/aleju/imgaug, last accessed Aug. 17, 2020, 25 pages.

Jin et al., "Introspective Classification with Convolutional Nets," 31st Conference on Neural Information Processing Systems, arXiv:1704.07816v2 [cs.CV], Jan. 5, 2018, 12 pages.

Dvornik et al., "On the Importance of Visual Context for Data Augmentation in Scene Understanding," arXiv:1809.02492v3 [cs.CV], Sep. 19, 2019, 15 pages.

"Data augmentation and effective class imbalance," https://stats.stackexchange.com/questions/317920/data-augmentation-and-effective-class-imbalance, last accessed Aug. 17, 2020, 2 pages.

* cited by examiner

SYNTHETIC TRAINING DATA GENERATION FOR IMPROVED MACHINE LEARNING MODEL GENERALIZABILITY

TECHNICAL FIELD

The subject disclosure relates generally to training of machine learning models, and more specifically to synthetic training data generation for improved machine learning model generalizability.

BACKGROUND

The efficacy and/or generalizability of a machine learning model depends upon the veracity, volume, variety, and/or velocity of the data on which the machine learning model is trained. In other words, the implementation of high quality, more voluminous, more varied/diverse, and/or more readily available training data can result in the creation of machine learning models that are invariant to various challenges faced in real-world operational scenarios. Conversely, the implementation of low quality, less voluminous, less varied/diverse, and/or less readily available training data can result in the creation of machine learning models that are easily impeded by various challenges faced in real-world operational scenarios. Thus, systems and/or techniques that can increase the veracity, volume, variety, and/or velocity of available training data can be desirable.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, devices, systems, computer-implemented methods, apparatus and/or computer program products that facilitate synthetic training data generation for improved machine learning model generalizability are provided.

According to one or more embodiments, a system is provided. The system can comprise a memory that can store computer-executable components. The system can further comprise a processor that can be operably coupled to the memory and that can execute the computer-executable components stored in the memory. In various embodiments, the computer-executable components can comprise an element augmentation component that can generate a set of preliminary annotated training images based on an annotated source image. In various aspects, a preliminary annotated training image can be formed by inserting at least one element of interest or at least one background element into the annotated source image. In various instances, the computer-executable components can comprise a modality augmentation component that can generate a set of intermediate annotated training images based on the set of preliminary annotated training images. In various cases, an intermediate annotated training image can be formed by varying at least one modality-based characteristic of a preliminary annotated training image. In various aspects, the computer-executable components can comprise a geometry augmentation component that can generate a set of deployable annotated training images based on the set of intermediate annotated training images. In various instances, a deployable annotated training image can be formed by varying at least one geometric characteristic of an intermediate annotated training image. In various embodiments, the computer-executable components can comprise a training component that can train a machine learning model on the set of deployable annotated training images.

According to one or more embodiments, the above-described system can be implemented as a computer-implemented method and/or a computer program product.

According to one or more embodiments, a computer program product can be provided. In various cases, the computer program product can comprise a computer readable memory having program instructions embodied therewith. In various cases, the program instructions can be executable by the processor to cause the processor to perform various operations. In some instances, such operations can comprise parametrizing a simulation space of data segments by defining a set of augmentation subspaces, wherein each augmentation subspace comprises a corresponding set of augmentable parameters. In various instances, each augmentable parameter can have a corresponding parametric range of possible values or states. In various aspects, the operations can further comprise receiving a source data segment. In various embodiments, the operations can further comprise, for each augmentable parameter, sampling a parametric range of possible values or states corresponding to the augmentable parameter. In some cases, this can yield a collection of sampled ranges of values or states that represents the simulation space. In various aspects, the operations can further comprise generating a set of training data segments by applying the collection of sampled ranges of values or states to copies of the source data segment.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
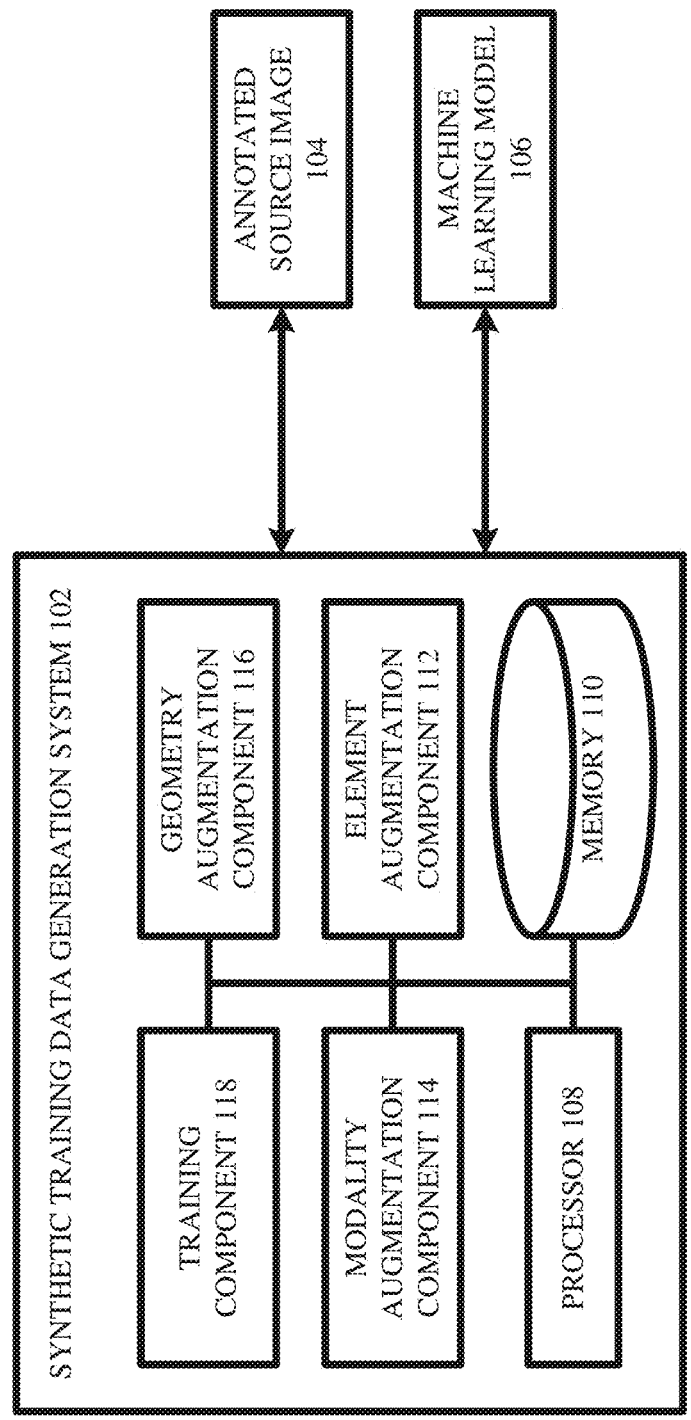
FIG. 1 illustrates a block diagram of an example, non-limiting system that facilitates synthetic training data generation for improved machine learning model generalizability in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

A machine learning model can be any suitable artificial intelligence model and/or algorithm that can map a set (e.g., one or more) of input variables to a set (e.g., one or more) of output variables. In various aspects, each of the output variables can be referred to as a class, a classification, a label, a category, a segmentation, a detection, and/or so on. In other words, a machine learning model can receive input data and can determine to which class the input data belongs (e.g., can classify the input data). In other cases, a machine learning model can produce as output any suitable segmentations, determinations, decisions, predictions, inferences, regressions, and/or so on. In various aspects, a machine learning model can be designed and/or configured to receive any suitable type of input data of any suitable dimensionality (e.g., scalars, vectors, matrices, and/or tensors) and to generate any suitable type of output data of any suitable dimensionality (e.g., scalars, vectors, matrices, and/or tensors). As some non-limiting examples, a machine learning model can be configured to perform image recognition, classification, and/or segmentation (e.g., recognizing character strings, numeric objects, and/or alphanumeric objects depicted in images; recognizing flora and/or fauna depicted in images; recognizing anatomical structures depicted in images; recognizing inanimate objects depicted in images), can be configured to perform sound recognition, classification, and/or segmentation (e.g., recognizing spoken letters, words, and/or speech present in audio data; recognizing voices present in audio data; recognizing sounds of fauna present in audio data; recognizing sounds of inanimate objects present in audio data), and/or any other suitable type of data recognition, classification, segmentation, prediction, determination, and/or detection (e.g., distinguishing spam emails from non-spam emails; distinguishing customers that are likely to transact from customers that are unlikely to transact; distinguishing transactions that are likely fraudulent from transactions that are unlikely fraudulent; and/or so on). In various aspects, any suitable output dimensionality can be implemented (e.g., binary classifications, tertiary classifications, quaternary classifications, and/or any suitable higher-order classifications).

In various aspects, a machine learning model can be trained (e.g., via supervised training, unsupervised training, and/or reinforcement learning) to classify, label, and/or make any other determinations, predictions, and/or inferences about received input data. When supervised training is implemented, each piece of training data can have a corresponding annotation. In various aspects, the corresponding annotation can indicate the true classification to which the piece of training data is known to belong (e.g., can represent a ground truth). During supervised training, the machine learning model can be fed a piece of training data, and the machine learning model can accordingly generate a resulting classification. In various cases, a difference between the resulting classification and the known annotation can be used (e.g., in back propagation) to update parameters of the machine learning model. Updating the parameters of the machine learning model in this way can help to cause the machine learning model to more accurately analyze future input data that is similar to the training data.

In various instances, the efficacy of a machine learning model can depend upon the quality of the training which the machine learning model undergoes. In other words, a machine learning model can perform better (e.g., can more accurately analyze input data) when the machine learning model is trained on better and/or higher quality training data. In various aspects, the quality of training data can be described in terms of veracity, volume, variety, and/or velocity. In various instances, the veracity of the training data can relate to the accuracy of the known annotations that correspond to the training data (e.g., parameters of a machine learning model can be accurately updated/adjusted only when accurate annotations of training data are involved; so, if the known annotations of the training data are not accurate, the training can be ineffective, and the machine learning model can fail to accurately analyze input data when the machine learning model is deployed in real-life). In various cases, the volume of the training data can relate to the amount of the training data (e.g., parameters of a machine learning model can be more fully/appropriately updated/adjusted when more training data is available; so, if little training data is available to feed to the machine learning model, the training can be ineffective, and the machine learning model can fail to accurately analyze input data when the machine learning model is deployed in real-life). In various aspects, the variety of the training data can relate to the feature diversity that is present within the training data (e.g., a machine learning model can be trained to detect and/or ignore only those features that are present within the training data; so, if there is not much real-world variety in the features depicted in the training data, the training can be ineffective, and the machine learning model can fail to accurately analyze input data when the machine learning model is deployed in real-life). In some instances, the velocity of the training data can relate to how quickly the training data and associated annotations can be collected from training data sources (e.g., a machine learning model can be trained only when annotated training data is available; so, if it takes days, weeks, or months to generate annotated training data, waiting days, weeks, or months can be required before training and/or deploying the machine learning model).

In short, inadequate training data can lead to inadequate machine learning models (e.g., there can be a 5% to 40% drop in performance accuracy when a model is operated on a dataset not represented by the training dataset). Thus, improving the veracity, volume, variety, and/or velocity of training data can help to improve the generalizability of a machine learning model. For example, a machine learning model that is trained on high veracity, high volume, high variety, and/or high velocity training data can accurately analyze input data regardless of real-world variability in the input data. Conversely, a machine learning model that is trained on low veracity, low volume, low variety, and/or low velocity training data can be easily thrown off by real-world variability in input data and thus can fail to accurately analyze the input data. In various aspects, systems and/or techniques that can improve veracity, volume, variety, and/or velocity of training data can thus be desirable.

Various embodiments of the subject innovation can address one or more of these issues/problems. One or more embodiments described herein include systems, computer-implemented methods, apparatus, and/or computer program products that can facilitate synthetic training data generation for improved machine learning model generalizability. In various instances, embodiments of the subject innovation can be considered as computerized tools for quickly generating veracious, voluminous, and/or varied training data for any suitable machine learning model. In various aspects, embodiments of the subject innovation can then train a machine learning model on the quickly generated, veracious, voluminous, and/or varied training data, thereby improving the efficacy and/or generalizability of the machine learning model.

For ease of explanation, the herein teachings regarding the quick generation of veracious, voluminous, and/or varied training data are discussed in relation to machine learning models that are configured to classify/label two-dimensional medical images in clinical contexts. However, it should be understood that this is exemplary and non-limiting. In various aspects, the herein teachings can be used to quickly generate veracious, voluminous, and/or varied training data for any suitable machine learning model that is configured to generate any suitable type of result (e.g., classification, segmentation, determination, inference, prediction, and/or so on) in any suitable operational context (e.g., machine learning models that are configured to receive two-dimensional and/or three-dimensional image data as input, machine learning models that are configured to receive one-dimensional and/or multi-dimensional sound data as input, and/or machine learning models that are configured to receive any other suitable data having any suitable dimensionality as input).

In various instances, embodiments of the subject innovation can electronically receive an annotated source image. In various aspects, the annotated source image can be a medical image of a patient (e.g., X-ray image of the patient, computed tomography (CT) image of the patient, magnetic resonance imaging (MRI) image of the patient, positron emission tomography (PET) image of the patient, visible-light-spectrum photograph of the patient, and/or so on). In various aspects, the annotated source image can be generated and/or captured by any suitable imaging device and/or apparatus, and the annotated source image can be received directly from the imaging device and/or apparatus. In various other aspects, the annotated source image can be stored in any suitable database and/or data structure, and the annotated source image can be retrieved from the database and/or data structure. In various cases, the annotated source image, as its name implies, can be associated with an annotation. In various aspects, the annotation can be any suitable indication of a class, classification, category, and/or label that is known to apply to the annotated source image (e.g., the annotation can indicate that the annotated source image depicts a patient with a brain lesion, the annotation can indicate that the annotated source image depicts a patient with tooth decay, the annotation can indicate that the annotated source image depicts a patient with a clogged blood vessel, the annotation can indicate that the annotated source image depicts a patient with a particular skin condition, the annotation can indicate that the annotated source image depicts a patient with lung cancer, and/or so on). In various aspects, the annotation can be at any suitable level of granularity and/or specificity (e.g., the annotation can indicate merely the condition afflicting the patient, and/or the annotation can more specifically indicate any other information that characterizes the condition afflicting the patient, such as localization/laterality of the condition, severity of the condition, age of the condition, prognosis associated with the condition, and/or so on). In various instances, the annotation can be generated and/or created by any suitable technique, such as manually by a clinician and/or medical professional.

As described herein, various embodiments of the subject innovation can electronically receive the annotated source image and can electronically generate a plurality of veracious, voluminous, and/or varied training images based on the annotated source image. In various aspects, this can be accomplished by copying the annotated source image and by performing three different types of augmentations on the copies of the annotated source image.

Specifically, in various instances, embodiments of the subject innovation can generate, via an element augmentation component, a set of preliminary annotated training images (e.g., also referred to as preliminary training images) based on the annotated source image. In various aspects, a preliminary annotated training image can be formed by inserting into the annotated source image at least one element/feature of interest and/or at least one background element/feature. In various aspects, an element/feature of interest (at least with respect to images) can be any suitable visual object and/or visual characteristic which can be added to the annotated source image (e.g., which can be added to a copy of the annotated source image) and which is an element/feature that the machine learning model to be trained is supposed to learn, predict, detect, and/or classify. For example, if the machine learning model to be trained is supposed to learn, predict, detect, and/or classify different types of brain lesions, an element/feature of interest can be a stand-alone image of a particular brain lesion that is insertable into the annotated source image. As another example, if the machine learning model to be trained is supposed to learn, predict, detect, and/or classify skin growths, an element/feature of interest can be a stand-alone image of a particular skin growth that is insertable into the annotated source image. In some cases, an element/feature of interest can be referred to as a positive element/feature. In various aspects, a background element/feature (at least with respect to images) can be any suitable visual object and/or visual characteristic which can be added to the annotated source image (e.g., which can be added to a copy of the annotated source image) and which is an element/feature that the machine learning model to be trained is not supposed to learn, predict, detect, and/or classify. Instead, in various cases, a background element/feature can negatively affect classifications generated by the machine learning model (e.g., can distract and/or throw off the machine learning model). For example, if the machine learning model to be trained is supposed to learn, predict, detect, and/or classify a particular type of morbidity, a background element/feature can be a stand-alone image of an unrelated co-morbidity that is insertable into the annotated source image. As another example, in some cases, a background element/feature can be a stand-alone image of a particular piece of medical equipment that is insertable into the annotated source image. In various cases, when an element/feature is inserted into a copy of the annotated source image, the copy can now be referred to as a preliminary training image. In various aspects, any suitable number of preliminary training images can be generated based on the annotated source image.

In various instances, different elements/features can be differently localized and/or positioned within the annotated source image (e.g., within a copy of the annotated source image) in different ways, thereby yielding different preliminary training images. In some cases, inserted elements/features can be randomly localized and/or positioned in the annotated source image within any suitable range of biologically-possible locations/positions. For instance, suppose that the annotated source image is an X-ray of a patient's chest and abdomen. Accordingly, the annotated source image can depict the ribcage of the patient, the chest cavity of the patient, the intestinal/abdominal cavity of the patient, and/or so on. Further, suppose that the machine learning model to be trained is supposed to learn, predict, detect, and/or classify lung cancers (and/or to otherwise perform lung segmentation). In various aspects, an element/feature can be added to and/or inserted into the annotated source image in any biologically-possible location/position. For example, suppose that the element/feature is a cancerous lung growth (e.g., an element/feature of interest). In various aspects, a first copy of the X-ray can be made, and the cancerous lung growth can be inserted into the first copy in any suitable location within the depicted chest cavity and can be not inserted into the depicted abdominal cavity (e.g., a cancerous lung growth can possibly form in the lungs and thus in the chest cavity of a patient; however, a cancerous lung growth cannot possibly form in the abdominal cavity of the patient). In various cases, the first copy can now be considered as a first preliminary training image. As another example, suppose that the element/feature is stomach gas (e.g., a background element/feature). In various aspects, a second copy of the X-ray can be made, and the stomach gas can be inserted into the second copy in any suitable location within the depicted abdominal cavity and can be not inserted into the depicted chest cavity (e.g., stomach gas can possibly form in the abdominal cavity of a patient; however, stomach gas cannot possibly form in the chest cavity of the patient). In this way, an insertable element/feature can be localized in any suitable, biologically-possible location/position in the annotated source image. In various cases, the second copy can now be considered as a second preliminary training image. Thus, different preliminary training images can be formed by inserting different elements/features into the annotated source image (e.g., into copies of the annotated source image).

In various aspects, a same element/feature can be differently localized within the annotated source image (e.g., within copies of the annotated source image), thereby yielding different preliminary training images. For instance, consider again the example above where the first preliminary training image includes an inserted cancerous lung growth. Suppose that the cancerous lung growth is inserted in a top portion of a right lung in the depicted chest cavity of the patient. In some cases, a third copy of the X-ray can be made, and the cancerous lung growth can be inserted into a bottom portion of a left lung in the depicted chest cavity. In various aspects, the third copy can now be considered as a third preliminary training image. Thus, both the first preliminary training image and the third preliminary training image can be formed by inserting the image of the cancerous lung growth into the annotated source image, but they can be different preliminary training images because the cancerous lung growth can be localized differently in each. As another instance, consider again the example above where the second preliminary training image includes inserted stomach gas. Suppose that the stomach gas is inserted in a top-left portion of the depicted abdominal cavity of the patient. In some cases, a fourth copy of the X-ray can be made, and the stomach gas can be inserted into a bottom-right portion in the depicted abdominal cavity. In various aspects, the fourth copy can now be considered as a fourth preliminary training image. Thus, both the second preliminary training image and the fourth preliminary training image can be formed by inserting the image of the stomach gas into the annotated source image, but they can be different preliminary training images because the stomach gas can be localized differently in each. In this way, a same element/feature can be inserted into different copies of the annotated source image in different places/locations/positions, thereby yielding different preliminary training images.

It should be appreciated that any suitable characteristic of an insertable element/feature can be varied when inserting the element/feature into the annotated source image (e.g., into copies of the annotated source image). For instance, a same element/feature can be inserted into two different copies of the annotated source image, such that the same element/feature has different spatial dimensions (e.g., length, width, height, thickness), different spatial orientations (e.g., oriented upside-down, oriented sideways, oriented backwards), and/or different intensities in the different copies of the annotated source image.

Note that, when background elements/features are inserted, the preliminary training images generated based on the annotated source image can, in some cases, share the annotation of the annotated source image (e.g., the classification and/or label of a preliminary training image can be the same as the classification and/or label of the annotated source image when a background element/feature is inserted). For instance, suppose that the annotated source image depicts a chest X-ray of a patient, and suppose that the annotation indicates that the patient suffers from pneumonia. In such case, inserting background elements/features (e.g., stomach gas, medical cables/tubes/wires, a pacemaker, and/ or so on) does not change the fact that the patient suffers from pneumonia.

Note that, when elements/features of interest are inserted, the preliminary training images generated based on the annotated source image can, in some cases, have annotations that are based on the inserted elements/features of interest. For instance, suppose that the annotated source image depicts a head CT scan of a patient, and suppose that the annotation indicates that the patient suffers from a left-side occluded blood vessel. In such case, inserting elements/ features of interest can require a commensurate change/ update in the annotation. For instance, if another occluded blood vessel is inserted in a right side of a depicted cranial cavity, the annotation can be updated to indicate that there are both left-side and right-side occluded blood vessels in the updated image.

Thus, in various embodiments, an annotation of any preliminary training image can be known/created based on the annotation of the annotated source image and/or based on the elements/features inserted into the annotated source image.

In various aspects, a catalog of premade, pre-drawn, pre-illustrated, and/or pre-generated elements/features can be maintained, and any suitable number of premade, pre-drawn, pre-illustrated, and/or pre-generated elements/features from the catalog can be inserted into the annotated source image (e.g., into copies of the annotated source image) in any suitable locations and/or any suitable orientations to generate the set of preliminary training images. In various aspects, the catalog can be any suitable database and/or data structure (e.g., relational database, graph database, hybrid database). In various aspects, the elements/ features stored in the catalog can be created via any suitable technique (e.g., the elements/features stored in the catalog can be electronic copies of hand-drawn elements/features, can be electronic images of two-dimensional computer-aided-design models, can be two-dimensional computer-aided-design models themselves, can be two-dimensional projections of three-dimensional computer-aided-design models, can be three-dimensional computer-aided-design models themselves, and/or so on).

In the medical context, such permutatory insertion of elements/features can help to more fully simulate and/or approximate real-world biological variability (e.g., a single X-ray scan can fail to adequately represent the full space of biological variability experienced by real-world patients; so, to help simulate and/or span the full space of biological variability experienced by real-world patients, various biological structures and/or medical equipment structures can be added to and/or superimposed on the single X-ray scan and/or copies of the single X-ray scan).

In various instances, embodiments of the subject innovation can generate, via a modality augmentation component, a set of intermediate annotated training images (e.g., also referred to as intermediate training images) based on the set of preliminary training images. In various aspects, an intermediate training image can be formed by varying at least one modality-based characteristic of a preliminary training image. In various aspects, a modality-based characteristic (at least with respect to images) can be any suitable image property that depends upon the device modality (e.g., the image-capture device) that generated and/or captured the annotated source image. For example, different image-capture device modalities can exhibit different gamma/radiation levels, different brightness/contrast levels, different motion/ blur levels, different noise levels, different resolutions, different fields of view, different magnification levels, different visual textures, different imaging artifacts (e.g., glares; scratches, dust, and/or any other obscuring material on a camera lens), and/or so on. It should be understood that, in various aspects, some modality-based characteristics can vary continuously, while other modality-based characteristics can vary discretely. In various instances, an intermediate training image can be formed from a preliminary training image by changing the gamma/radiation level, the brightness/contrast level, the motion/blur level, the noise level, the resolution, the field of view, the magnification level, the visual texture, and/or the imaging artifacts of the preliminary training image. In various cases, any suitable number of intermediate training images can be formed from each preliminary training image by varying one or more modality-based characteristics of the preliminary training image. For instance, consider a preliminary training image (e.g., one among many generated from the annotated source image) exhibiting an existing gamma/radiation level. In various aspects, a first copy of the preliminary training image can be made, and the existing gamma/radiation level of the first copy can be changed to a first gamma/radiation level. In various cases, the first copy of the preliminary training image can now be considered a first intermediate training image. In various aspects, a second copy of the preliminary training image can be made, and the existing gamma/radiation level of the second copy can be changed to a second gamma/radiation level. In various cases, the second copy of the preliminary training image can now be considered a second intermediate training image. As another example, suppose that the preliminary training image exhibits an existing brightness/contrast level. In various aspects, a third copy of the preliminary training image can be made, and the existing brightness/contrast level of the third copy can be changed to a first brightness/contrast level. In various cases, the third copy of the preliminary training image can now be considered a third intermediate training image. In various aspects, a fourth copy of the preliminary training image can be made, and the existing brightness/contrast level of the fourth copy can be changed to a second brightness/contrast level. In various cases, the fourth copy of the preliminary training image can now be considered a fourth intermediate training image. As yet another example, suppose that the preliminary training image exhibits an existing glare. In various aspects, a fifth copy of the preliminary training image can be made, and the existing glare of the fifth copy can be removed, supplemented, and/or changed to a first glare. In various cases, the fifth copy of the preliminary training image can now be considered a fifth intermediate training image. In various aspects, a sixth copy of the preliminary training image can be made, and the existing glare of the sixth copy can be removed, supplemented, and/or changed to a second glare. In various cases, the sixth copy of the preliminary training image can now be considered a sixth intermediate training image. In this way, any suitable number of intermediate training images can be generated by varying in permutatory fashion at least one modality-based characteristic of each of the preliminary training images. In various cases, any suitable policy and/or scheme for varying modality-based characteristics of preliminary training images can be implemented.

In the medical context, such permutatory variation of modality-based characteristics can help to more fully simulate and/or approximate real-world device modality variability (e.g., a single X-ray scan can be generated by a single type/model of X-ray machine, and can thus fail to adequately represent the full space of X-ray machine variability present in real-world medical/clinical environments; so, to help simulate and/or span the full space of X-ray machine variability present in real-world medical/clinical environments, various modality-based characteristics of the single X-ray scan and/or copies of the single X-ray scan can be adjusted/changed).

In various aspects, embodiments of the subject innovation can generate, via a geometry augmentation component, a set of deployable annotated training images (e.g., also referred to as deployable training images) based on the set of intermediate training images. In various aspects, a deployable training image can be formed by applying at least one geometric transformation to an intermediate training image. In various aspects, a geometric transformation (at least with respect to images) can be any suitable mathematical transformation and/or operation that can spatially alter and/or transform an image pixel grid. For example, a geometric transformation can include reflecting an image about any suitable axis, rotating an image about any suitable axis, cropping any suitable portion of an image, panning an image, tilting an image, zooming in and/or out on an image, applying an affine and/or elastic transformation to an image, distorting an image away from rectilinear projection, and/or so on. In various instances, a deployable training image can be formed from an intermediate training image by flipping, rotating, cropping, panning, tilting, zooming, and/or distorting the intermediate training image. In various cases, any suitable number of deployable training images can be formed from each intermediate training image by applying one or more geometric transformations to the intermediate training image. For instance, consider an intermediate training image (e.g., one among many generated from the intermediate training images) exhibiting an existing orientation. In various aspects, a first copy of the intermediate training image can be made, and the existing orientation of the first copy can be reflected, rotated, panned, tilted, and/or zoomed to a first orientation. In various cases, the first copy of the intermediate training image can now be considered a first deployable training image. In various aspects, a second copy of the intermediate training image can be made, and the existing orientation of the second copy can be reflected, rotated, panned, tilted, and/or zoomed to a second orientation. In various cases, the second copy of the intermediate training image can now be considered a second deployable training image. As another example, suppose that the intermediate training image exhibits an existing appearance. In various aspects, a third copy of the intermediate training image can be made, and the existing appearance of the third copy can be distorted via a first affine and/or elastic transformation. In various cases, the third copy of the intermediate training image can now be considered a third deployable training image. In various aspects, a fourth copy of the intermediate training image can be made, and the existing appearance of the fourth copy can be distorted via a second affine and/or elastic transformation. In various cases, the fourth copy of the intermediate training image can now be considered a fourth deployable training image. In this way, any suitable number of intermediate training images can be generated by varying at least one modality-based characteristic of each of the preliminary training images. In various cases, any suitable policy and/or scheme for applying geometric transformations to intermediate training images can be implemented.

In the medical context, such permutatory application of geometric transformations can help to more fully simulate and/or approximate real-world image variability (e.g., a single X-ray scan can have certain geometric characteristics, and can thus fail to adequately represent the full space of X-ray characteristics present in real-world medical/clinical environments; so, to help simulate and/or span the full space of X-ray characteristics present in real-world medical/clinical environments, various geometric transformations can be applied to the single X-ray scan and/or copies of the single X-ray scan).

In various instances, embodiments of the subject innovation can train, via a training component, a machine learning model on the set of deployable training images. Note that, as described herein, a single annotated source image can be used to automatically and quickly generate a plurality of deployable training images. Specifically, the plurality of deployable training images can be formed by making different copies of the annotated source image, by inserting into the different copies different elements/features in different locations/orientations, by altering different modality-based characteristics of the different copies, by differently altering same modality-based characteristics of the different copies, and/or by applying different combinations of geometric transformations to the different copies. In other words, a single annotated source image can be used to create a plurality of synthetically-generated training images that help to account for real-world variability through element/feature insertion, through modality-based modulation, and/or through geometric transformations (e.g., there can exist many permutations of different insertable elements/features, different insertion locations and/or orientations and/or dimensions, different modality-based characteristics, and/or different geometric transformations). Thus, training a machine learning model on the plurality of deployable training images can improve performance and/or efficacy of the machine learning model as compared to training on the single annotated source image alone.

To help clarify some of the above discussion, consider the following non-limiting example. Suppose that it is desired to train a machine learning model on an initial training dataset. Further, suppose that the initial training dataset includes an annotated chest X-ray image (e.g., source image) that is received from an X-ray machine, and suppose that the machine learning model is supposed to learn, predict, detect, and/or classify lung cancer in chest X-ray images. In various aspects, a set of preliminary training X-ray images can be formed based on inserting various elements/features into the annotated chest X-ray image. For instance, in some cases, a first preliminary training X-ray image can be formed by inserting an image of a pacemaker in a heart-location of the annotated chest X-ray image, a second preliminary training X-ray image can be formed by placing an image of medical tubing in an upper-left portion of the annotated chest X-ray image, a third preliminary training X-ray image can be formed by inserting the image of the medical tubing in an upper-right portion of the annotated chest X-ray image (e.g., same element orientation, different location), a fourth preliminary training X-ray image can be formed by inserting a differently oriented/sized image of the medical tubing in an upper-left portion of the annotated chest X-ray image (e.g., different element orientation/dimensions, same location), a fifth preliminary training X-ray image can be formed by inserting an image of stomach gas into a lower portion of the annotated chest X-ray image, and a sixth preliminary training X-ray image can be formed by inserting no elements/features into the annotated chest X-ray. That is, in various cases, element/feature insertion can be implemented to generate six preliminary training X-ray images based on the single annotated X-ray image.

In various aspects, a set of intermediate training X-ray images can be formed based on adjusting various modality-based characteristics of each of the six preliminary training X-ray images. For instance, in some cases, suppose that there are three possible gamma/radiation levels which can be exhibited in an X-ray image (e.g., high gamma/radiation, medium gamma/radiation, low gamma/radiation), suppose that there are three possible blur levels which can be exhibited in an X-ray image (e.g., high blur, medium blur, low blur), and suppose that there are two possible artifacts which can be exhibited in an X-ray image (e.g., lens glare vs. no lens glare). In such case, eighteen intermediate training X-ray images can be formed from each of the preliminary training X-ray images (e.g., three gamma/radiation levels multiplied by three blur levels multiplied by two artifact levels), for a total of one hundred eight intermediate training X-ray images (e.g., eighteen intermediate training X-ray images per preliminary training X-ray image multiplied by six preliminary training X-ray images).

In various aspects, a set of deployable training X-ray images can be formed based on applying various geometric transformations to each of the intermediate training X-ray images. For instance, in some cases, suppose that available geometric transformations include three potential reflections (e.g., reflecting about a horizontal axis, reflecting about a vertical axis, and/or not reflecting at all), four potential rotations (e.g., rotating clockwise by 15 degrees, rotating clockwise by 45 degrees, rotating clockwise by 75 degrees, and/or not rotating at all), two possible crops (e.g., applying a central crop vs. not applying a central crop), and two possible distortions (e.g., applying a barrel distortion vs. not applying a barrel distortion). In such case, forty-eight different deployable training X-ray images can be formed from each intermediate training X-ray image (e.g., three possible reflections multiplied by four possible rotations multiplied by two possible crops multiplied by two possible distortions), for a total of 5,184 deployable training X-ray images (e.g., forty-eight deployable training X-ray images per intermediate training X-ray image multiplied by one hundred eight intermediate training X-ray images). That is, by applying the teachings disclosed herein, a single annotated X-ray image in the initial training dataset can be leveraged to synthetically generate very many (e.g., 5,184) deployable training X-ray images which simulate real-world variety and on which the machine learning model can be trained. If the initial training dataset includes one hundred annotated X-ray images instead of just one, various embodiments of the subject innovation can thus generate 518,400 deployable training X-ray images (e.g., 5,184 deployable training X-ray images per annotated X-ray image in the initial training dataset multiplied by 100 annotated X-ray images in the initial training dataset). In various aspects, training the machine learning model on the set of deployable training X-ray images can yield significantly improved efficacy and/or performance as compared to training the machine learning model only on the initial training dataset. Indeed, by inserting various elements/features, by varying different modality-based characteristics, and/or by applying different geometric transformations, embodiments of the subject innovation can electronically create a set of training data which can cause a machine learning model to become invariant to and/or robust against such various elements/features, different modality-based characteristics, and/or different geometric transformations.

It should be appreciated that the numbers and/or details in the above example are exemplary, non-limiting, and for purposes of illustration.

Various embodiments of the subject innovation can be employed to use hardware and/or software to solve problems that are highly technical in nature (e.g., to facilitate synthetic training data generation for improved machine learning model generalizability), that are not abstract and that cannot be performed as a set of mental acts by a human. Further, some of the processes performed can be performed by a specialized computer (e.g., trained machine learning model) for carrying out defined tasks related to synthetic training data generation for improved machine learning model generalizability (e.g., generating a set of preliminary annotated training images based on an annotated source image, wherein a preliminary annotated training image is formed by inserting at least one element of interest or at least one background element into the annotated source image; generating a set of intermediate annotated training images based on the set of preliminary annotated training images, wherein an intermediate annotated training image is formed by varying at least one modality-based characteristic of a preliminary annotated training image; generating a set of deployable annotated training images based on the set of intermediate annotated training images, wherein a deployable annotated training image is formed by varying at least one geometric characteristic of an intermediate annotated training image; and training a machine learning model on the set of deployable annotated training images). Such defined tasks are not conventionally performed manually by humans. Moreover, neither the human mind nor a human with pen and paper can electronically insert elements/features into an image, can electronically vary modality-based characteristics of an image, or can electronically adjust geometric characteristics of an image. Instead, various embodiments of the subject innovation are inherently and inextricably tied to computer technology and cannot be implemented outside of a computing environment (e.g., embodiments of the subject innovation constitute a computerized device that synthetically generates many varied training images based on a given annotated source image; such a computerized device can exist only in a computing environment).

In various instances, embodiments of the invention can integrate into a practical application the disclosed teachings regarding synthetic training data generation for improved machine learning model generalizability. Indeed, in various embodiments, the disclosed teachings can provide a computerized system that receives as input one or more annotated source images (e.g., real-world medical/clinical images of patients that have associated annotations created by real-world medical/clinical professionals) and that produces as output a plurality of training images based on the one or more annotated source images, where the plurality of training images are formed by copying the one or more annotated source images, by electronically inserting elements/features of interest and/or background elements/features into the copies, by electronically varying modality-based characteristics of the copies, and/or by electronically applying geometric transformations to the copies. The resulting plurality of training images are a highly varied set of images that approximate and/or simulate real-world variability (e.g., element/feature insertion can help to approximate real-world biological variability; modality-based characteristic variation can help to approximate real-world device modality variability; and geometric characteristic variation can help to further approximate real-world variability). Training a machine learning model on such a plurality of training images can result in significantly improved performance and/or efficacy as compared to training a machine learning model only on the one or more annotated source images. So, such a computerized system is clearly a useful and practical application of computers.

Moreover, various embodiments of the invention can provide technical improvements to and solve problems that arise in the field of training of machine learning models. As explained above, the efficacy and/or performance of a machine learning model can be limited by the veracity, volume, variety, and/or velocity of training data (e.g., training data that inadequately simulates real-world variability can result in inadequate machine learning models). Embodiments of the subject innovation address this technical problem by providing a computerized system that can quickly synthetically generate veracious, voluminous, and/or varied training data (e.g., element/feature insertion, modality-based characteristic variation, and geometric transformations can all help to simulate and/or approximate real-world variability). Training a machine learning model on such veracious, voluminous, and/or varied training data can result in significantly improved model performance. Because embodiments of the subject innovation can improve the very computing performance of machine learning models, embodiments of the subject innovation constitute a technical improvement.

Furthermore, various embodiments of the subject innovation can control real-world devices based on the disclosed teachings. For example, embodiments of the subject innovation can electronically receive a real-world annotated source image (e.g., X-ray scan, CT scan, MRI scan, PET scan, ultrasound scan, visible-light-spectrum photograph). Embodiments of the subject innovation can electronically insert real-world images of elements/features of interest and/or real-world images of background elements/features into the real-world annotated source image. Embodiments of the subject innovation can electronically vary real-world modality-based characteristics of the real-world annotated source image. Moreover, embodiments of the subject innovation can electronically vary real-world geometric characteristics of the real-world annotated source image. Such electronic insertions and/or electronic variations can result in a plurality of real-world training images that more fully and/or more completely simulate real-world image variability. Training a real-world machine learning model on such a plurality of real-world training images can result in enhanced efficacy/performance of the machine learning model, which is a concrete and tangible technical improvement.

It should be appreciated that the herein figures are exemplary and non-limiting.

FIG. 1 illustrates a block diagram of an example, non-limiting system 100 that can facilitate synthetic training data generation for improved machine learning model generalizability in accordance with one or more embodiments described herein. As shown, it can be desired to train a machine learning model 106 on an annotated source image 104. However, the annotated source image 104 can, in various aspects, fail to fully and/or adequately represent the full space of real-world image variability. In various instances, a synthetic training data generation system 102 can address this problem by electronically generating a set of training images based on the annotated source image 104 and on which the machine learning model 106 can be trained.

In various aspects, the machine learning model 106 can be any suitable computationally-implemented artificial intelligence model and/or algorithm that is designed to receive as input one or more images and to produce as output one or more classifications, labels, and/or predictions based on the inputted one or more images (e.g., support vector machine, neural network, expert system, Bayesian belief network, fuzzy logic, data fusion engine, and/or so on). In various aspects, any suitable machine learning model and/or algorithm can be implemented, such as a model and/or algorithm for performing classifications, for performing segmentations, for performing detections, for performing regressions, for performing reconstructions, for performing image-to-image (and/or data-to-data) transformations, and/or for performing any other suitable machine learning functionality.

In various aspects, the annotated source image 104 can be any suitable image which the machine learning model 106 is designed to analyze. For example, if the machine learning model 106 is designed to classify medical images, the annotated source image 104 can be any suitable medical image (e.g., X-ray scan of a patient, CT scan of a patient, MRI scan of a patient, PET scan of a patient, ultrasound scan of a patient, visible-light-spectrum photograph of a patient). As explained above, the annotated source image 104 can have a corresponding and/or associated annotation (e.g., a classification and/or label that is considered a ground truth for the annotated source image 104).

In various embodiments, the synthetic training data generation system 102 can electronically receive/retrieve (e.g., via any suitable wired and/or wireless electronic connection) the annotated source image 104. In various aspects, the synthetic training data generation system 102 can electronically receive/retrieve the annotated source image 104 from any suitable database and/or data structure that is accessible to the synthetic training data generation system 102. In various aspects, the synthetic training data generation system 102 can electronically receive/retrieve the annotated source image 104 directly from an image-capture device that generates, captures, and/or creates the annotated source image 104 (e.g., directly from an X-ray scanner, from a CT scanner, from a PET scanner, from an MRI scanner)

In various embodiments, the synthetic training data generation system 102 can comprise a processor 108 (e.g., computer processing unit, microprocessor) and a computer-readable memory 110 that is operably and/or operatively and/or communicatively connected/coupled to the processor 108. The memory 110 can store computer-executable instructions which, upon execution by the processor 108, can cause the processor 108 and/or other components of the synthetic training data generation system 102 (e.g., element augmentation component 112, modality augmentation component 114, geometry augmentation component 116, training component 118) to perform one or more acts. In various embodiments, the memory 110 can store computer-executable components (e.g., element augmentation component 112, modality augmentation component 114, geometry augmentation component 116, training component 118), and the processor 108 can execute the computer-executable components.

In various embodiments, the synthetic training data generation system 102 can comprise an element augmentation component 112. In various aspects, the element augmentation component 112 can generate a set of preliminary training images based on the annotated source image 104. Specifically, the element augmentation component 112 can comprise an element catalog that electronically stores images of elements (e.g., elements of interest and/or background elements) that are insertable into the annotated source image 104 (e.g., insertable into copies of the annotated source image 104). In various aspects, the element augmentation component 112 can form/generate a preliminary training image by making an electronic copy of the annotated source image 104 and by inserting at least one element from the element catalog into the electronic copy of the annotated source image 104.

It should be appreciated that when the herein disclosure discusses inserting elements into the annotated source image 104, this can include inserting elements into one or more copies of the annotated source image 104.

In various instances, the elements that are stored within the element catalog can depend upon the nature of the machine learning model 106. For example, the element catalog can include images of elements of interest and can include images of background elements. In various aspects, an element of interest can be any suitable visual object that the machine learning model 106 is supposed to learn, predict, detect, and/or classify. In various cases, a background element can be any suitable visual object that the machine learning model 106 need not learn, predict, detect, and/or classify, but which can impede and/or throw off the machine learning model 106. For example, if the machine learning model 106 is configured to learn, predict, detect, and/or classify lung growths, elements of interest can include various malignant lung growths and/or various benign lung growths, and background elements can include various medical equipment (e.g., pacemaker, intravenous tubing, stents, implants, electrocardiogram leads), various co-morbidities (e.g., heart defects, occluded blood vessels), stomach gas, and/or so on. In other words, in the medical context, an element of interest can be any suitable anatomical structure and/or biological symptom manifestation that the machine learning model 106 is supposed to learn, predict, and/or detect, and a background element can be any other suitable anatomical structure and/or biological symptom manifestation which can distract and/or impede the machine learning model 106 and/or can be any suitable piece of medical equipment which can distract and/or impede the machine learning model 106.

In various aspects, the element augmentation component 112 can insert any suitable combination of elements from the element catalog into the annotated source image 104 to create a preliminary training image (e.g., each preliminary training image can have one inserted element, each preliminary training image can have multiple inserted elements, different preliminary training images can have different numbers of inserted elements, and/or at least one preliminary training image can have no inserted elements).

In various aspects, the element augmentation component 112 can localize an inserted element in the annotated source image 104 in any suitable, biologically-possible location/position. For instance, if an image of a lung lesion is inserted by the element augmentation component 112, the image of the lung lesion can be placed in a depicted chest cavity of the annotated source image 104 and can avoid being placed in a depicted abdominal cavity of the annotated source image 104 (e.g., lung lesions can possibly form in the chest cavity but cannot possibly form in the abdominal cavity). In this way, a same element can be inputted into different locations/positions of the annotated source image 104, thereby yielding different preliminary training images.

In various instances, the element augmentation component 112 can control the orientation of an inserted element in the annotated source image 104. For example, if an image of a lung lesion is inserted by the element augmentation component 112, the image can be oriented as depicted in the element catalog, can be oriented upside-down, can be oriented backwards, can be oriented sideways, can be reflected/rotated in any suitable manner, and/or so on. In this way, a same element can be differently oriented in a same location of the annotated source image 104, thereby yielding different preliminary training images.

In some cases, the element augmentation component 112 can control dimensions and/or intensities of an inserted element in the annotated source image 104. For example, if an image of a lung lesion if inserted by the element augmentation component 112, the image of the lung lesion can be expanded, contracted, lengthened, widened, thickened, manipulated in any other suitable way, and/or so on. In this way, a same element can be differently sized in a same location and/or same orientation of the annotated source image 104, thereby yielding different preliminary training images.

In various instances, when a preliminary training image is formed by inserting only background elements into the annotated source image 104, an annotation of the preliminary training image can be the same as the annotation of the annotated source image 104 (e.g., if an X-ray image is annotated as depicting one type of lung cancer, adding stomach gas to that X-ray image can fail to affect the accuracy/completeness of the annotation). In various aspects, when a preliminary training image is formed by inserting an element of interest into the annotated source image 104, an annotation of the preliminary training image can be initialized as the annotation of the annotated source image 104 and can then be updated based on the inserted element of interest (e.g., if an X-ray image is annotated as depicting one type of lung cancer, adding a second type of lung cancer to that X-ray image can affect the accuracy/completeness of the annotation; accordingly, the annotation can be updated to indicate that the X-ray image now depicts two types of lung cancers).

In various embodiments, the synthetic training data generation system 102 can comprise a modality augmentation component 114. In various aspects, the modality augmentation component 114 can generate a set of intermediate training images based on the set of preliminary training images generated by the element augmentation component 112. Specifically, the modality augmentation component 114 can comprise a list of various modality-based characteristics. In various aspects, a modality-based characteristic can be any suitable image property that is related to and/or dependent upon a device modality that captured and/or generated the annotated source image 104. For example, modality-based characteristics can include gamma/radiation levels (e.g., since gamma/radiation is used to generate X-rays and/or CT scans), brightness levels, contrast levels, blur levels, noise levels, image texture, image field of view, image resolution, and/or image artifacts (e.g., glare on lens, scratch on lens, dust on lens). In other words, modality-based characteristics can represent parameters of image-capture devices, which parameters can affect the quality/properties of the captured images. In various cases, the modality augmentation component 114 can form/generate an intermediate training image by making an electronic copy of a preliminary training image and by varying/adjusting at least one modality-based characteristic of the preliminary training image.

It should be appreciated that when the herein disclosure discusses varying modality-based characteristics of a preliminary training image, this can include varying modality-based characteristics of an electronic copy of the preliminary training image.

In various aspects, the modality augmentation component 114 can vary/adjust/manipulate/modify any suitable combination of modality-based characteristics of a preliminary training image to create an intermediate training image (e.g., each intermediate training image can be formed by varying one modality-based characteristic, each intermediate training image can be formed by varying multiple modality-based characteristics, different intermediate training images can be formed by varying different numbers of modality-based characteristics, and/or at least one intermediate training image can involve no variation of any modality-based characteristics).

In various instances, varying and/or modifying modality-based characteristics can have no effect on the accuracy and/or completeness of annotations. Accordingly, an intermediate training image that is formed from a preliminary training image can have the same annotation as the preliminary training image.

In various embodiments, the synthetic training data generation system 102 can comprise a geometry augmentation component 116. In various aspects, the geometry augmentation component 116 can generate a set of deployable training images based on the set of intermediate training images generated by the modality augmentation component 114. Specifically, the geometry augmentation component 116 can comprise a list of various geometric transformations that can be applied to an image. In various aspects, a geometric transformation can be any suitable mathematical operation that can transform spatial properties of an image. For example, geometric transformations can include reflections of an image about any suitable axis, rotations of an image about any suitable axis, panning and/or tilting an image to change a two-dimensional projection and/or perspective of the image, cropping any suitable portion of an image, zooming in and/or out on an image, optically distorting an image (e.g., barrel distortion, pincushion distortion, mustache distortion, and/or any other suitable distortion away from a rectilinear projection), and/or so on. In various cases, the geometry augmentation component 116 can form/generate a deployable training image by making an electronic copy of an intermediate training image and by applying at least one geometric transformation to the electronic copy of the intermediate training image.

It should be appreciated that when the herein disclosure discusses applying geometric transformations to an intermediate training image, this can include applying geometric transformations to an electronic copy of the intermediate training image.

In various aspects, the geometry augmentation component 116 can apply any suitable combination of geometric transformations to an intermediate training image to create a deployable training image (e.g., each deployable training image can be formed by applying one geometric transformation, each deployable training image can be formed by applying multiple geometric transformations, different deployable training images can be formed by applying different numbers of geometric transformations, and/or at least one deployable training image can undergo no geometric transformations).

In various instances, applying geometric transformations can have no effect on the accuracy and/or completeness of annotations. Accordingly, a deployable training image that is formed from an intermediate training image can have the same annotation as the intermediate training image.

In various embodiments, the synthetic training data generation system 102 can comprise a training component 118. In various aspects, the training component 118 can actually train (e.g., via backpropagation and/or any other suitable technique) the machine learning model 106 on the set of deployable training images generated by the synthetic training data generation system 102.

Figure 2:
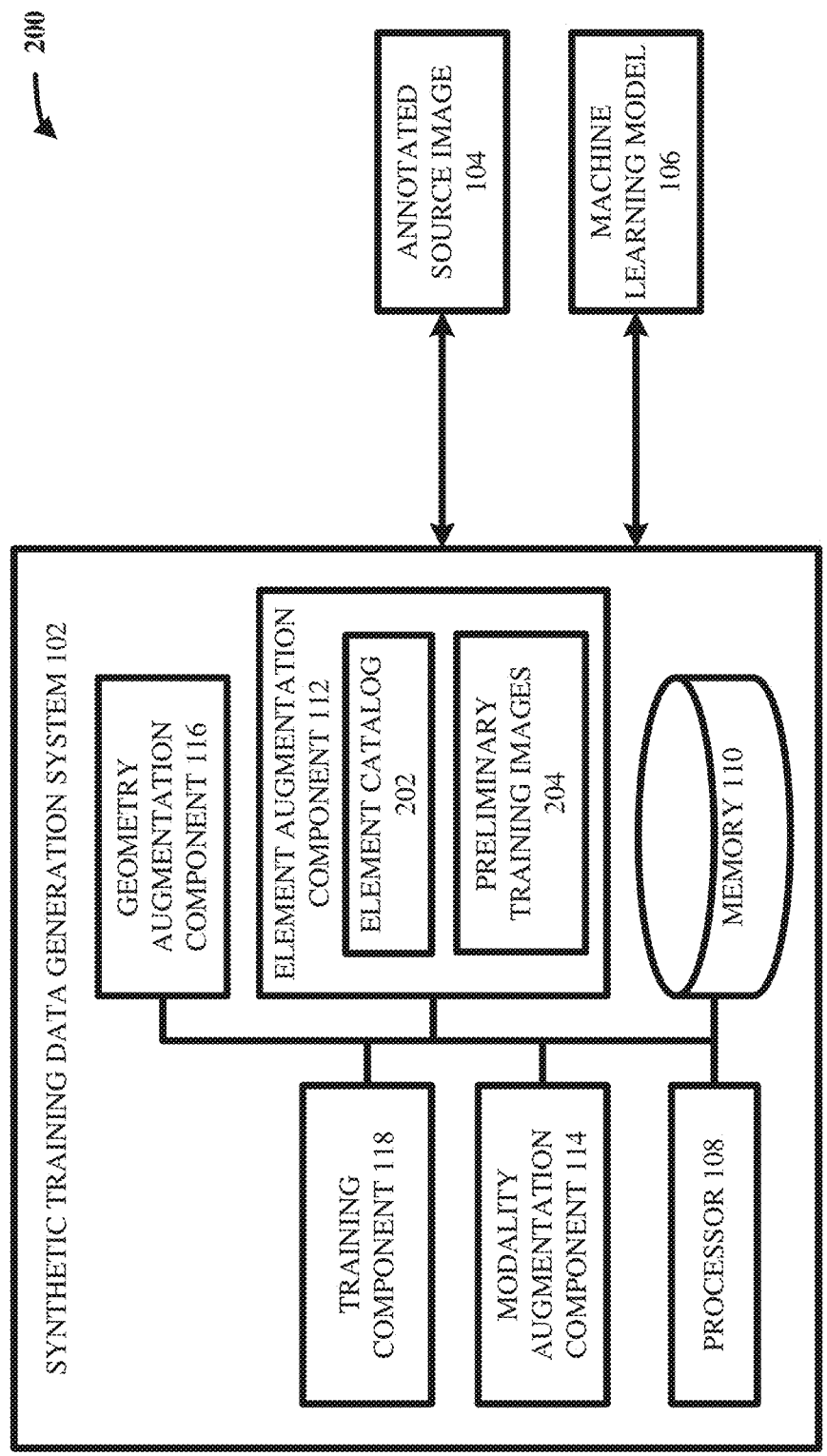
FIG. 2 illustrates a block diagram of an example, non-limiting system including an element catalog that facilitates synthetic training data generation for improved machine learning model generalizability in accordance with one or more embodiments described herein.

FIG. 2 illustrates a block diagram of an example, non-limiting system 200 including an element catalog that can facilitate synthetic training data generation for improved machine learning model generalizability in accordance with one or more embodiments described herein. As shown, the system 200 can, in some cases, comprise the same components as the system 100, and can further comprise an element catalog 202 and preliminary training images 204.

In various aspects, the element augmentation component 112 can comprise the element catalog 202. In various instances, the element augmentation component 112 can leverage the element catalog 202 to generate preliminary training images 204 based on the annotated source image 104. As mentioned above, the element catalog 202 can electronically store and/or maintain images of elements/features that are insertable into the annotated source image 104. Specifically, the element catalog 202 can include elements of interest and/or background elements. In various cases, an element interest can be any suitable visual object that the machine learning model 106 is supposed to learn, predict, and/or detect (e.g., if the machine learning model 106 is configured to detect occluded blood vessels in a patient's brain, elements of interest can be various images of occluded blood vessels). In various aspects, a background element can be any suitable visual object that can impede and/or distract the machine learning model 106 (e.g., if the machine learning model 106 is configured to detect occluded blood vessels in a patient's brain, background elements can be various images of brain lesions and/or various images of cranial and/or cerebral implants).

In various instances, the elements stored in the element catalog 202 can be generated via any suitable technique and/or can be stored in any suitable computerized format. In some cases, elements stored within the element catalog 202 can be scanned images of hand-drawn figures (e.g., a medical professional can sketch a brain lesion, a lung nodule, and/or intravenous tubing by hand, and the sketch and can be scanned and saved electronically within the element catalog 202). In some cases, elements stored within the element catalog 202 can be two-dimensional and/or three-dimensional computer-aided-design models (e.g., a medical professional can generate on a computer a two-dimensional and/or three-dimensional computer-aided-design model of a brain lesion, a lung nodule, and/or intravenous tubing, and the two-dimensional and/or three-dimensional computer-aided-design model can be saved and/or stored electronically within the element catalog 202). In various aspects, any other suitable technique can be implemented to generate and/or obtain the elements within the element catalog 202 (e.g., elements within the element catalog 202 can be cut-outs from existing images, and/or so on).

In various aspects, as mentioned above, the element augmentation component 112 can control and/or manipulate any suitable visual characteristics of the elements within the element catalog 202. For example, the element augmentation component 112 can change/modify any suitable spatial dimensions of the elements in the element catalog 202 (e.g., length, width, height, thickness, color, shading, intensity, and/or so on). As another example, the element augmentation component 112 can change/modify depicted and/or projected orientations of the elements in the element catalog 202 (e.g., can depict the elements facing forward, facing backward, facing upside down, facing sideways, rotated by any suitable magnitude about any suitable axis, reflected about any suitable axis, and/or so on). In various aspects, modifying/changing dimensions and/or orientations can be more realistically and/or more fully facilitated if computer-aided-design models are implemented, as mentioned above.

In various cases, as explained above, the element augmentation component 112 can localize an inserted element within the annotated source image 104 in any suitable, biologically-possible location (e.g., stomach gas can be inserted into any portion of a depicted abdominal cavity, but cannot be inserted into any portion of a depicted chest cavity). Thus, in various aspects, the element catalog 202 can map and/or correlate different elements with different biologically-possible locations, and the element augmentation component 112 can localization elements during insertion based on the mapping and/or correlation.

In various aspects, the element augmentation component 112 can insert elements into the annotated source image 104 according to any suitable augmentation policy and/or scheme.

In various instances, the element catalog 202 can be considered as a parametrization of the space of possible/potential elements/features that are insertable into the annotated source image 104. In other words, a space of all possible/potential image elements/features which can be depicted in the annotated source image 104 can be conceived, and the element catalog 202 can be constructed and/or configured so as to span and/or substantially span that space. In various cases, such a parametrized space can depend upon the operational context of the machine learning model 106 (e.g., in the medical context, the space can comprise possible/potential biological symptom manifestations that can be captured in an image and/or possible/potential medical equipment that can be captured in an image).

In various embodiments, the element augmentation component 112 can update and/or change the element catalog 202 (e.g., can update and/or change the images listed/stored in the element catalog 202 that are used to generate the preliminary training images 204). For instance, in some cases, the element catalog 202 can be initialized with an existing set of images of interest and/or an existing set of images of background elements. However, in various aspects, the element augmentation component 112 can periodically and/or aperiodically query any suitable database and/or data structure which is accessible to the element augmentation component 112 to check if new images of elements of interest and/or new images of background elements are available (e.g., to check if images that are not already stored/listed within the element catalog 202 are available for retrieval and/or download so that such new images can be used to generate the preliminary training images 204). If such new images of elements of interest and/or background elements are available in the database and/or data structure, the element augmentation component 112 can retrieve such new images and add them to the element catalog 202 and can thus begin inserting such new images into the annotated source image 104 to generate the preliminary training images 204. As another example, the element augmentation component 112 can receive input from an operator, which input includes a new image of an element of interest and/or background element that is not already stored/listed in the element catalog 202. In various aspects, the element augmentation component 112 can accordingly add the new image to the element catalog 202 and can thus begin using the new image to generate the preliminary training images 204. In this way, the element catalog 202 can be updated, changed, amended, edited, and/or modified as desired so as to suit different operational contexts.

As an example, suppose that the element catalog 202 includes an image of a lung nodule, an image of stomach gas, and an image of breathing tubes. Thus, the element augmentation component 112 can insert into the annotated source image 104 different combinations/permutations of the image of the lung nodule, the image of stomach gas, and the image of breathing tubes (e.g., with different localizations and/or orientations and/or dimensions) to generate the preliminary training images 204. In various aspects, the element augmentation component 112 can retrieve from any suitable database and/or data structure (and/or can receive as input from an operator) an image of a pacemaker. Since the image of the pacemaker is not already stored/listed within the element catalog 202, the element augmentation component 112 can add the image of the pacemaker to the element catalog 202. Thus, the element augmentation component 112 can begin inserting the image of the pacemaker (e.g., with different localizations and/or different orientations and/or different dimensions) into the annotated source image 104 to generate the preliminary training images 204. In this way, the element catalog 202 can be updated and/or enlarged over time and/or as desired.

Figure 3:
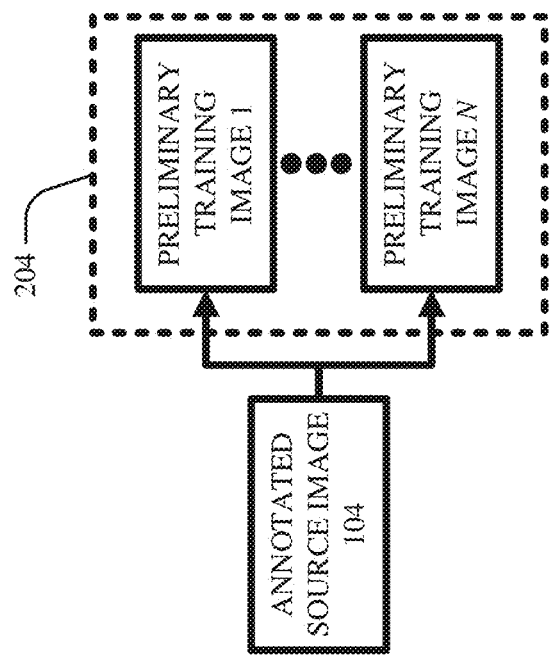
FIGS. 3-4 illustrate block diagrams of example, non-limiting preliminary training images formed from an annotated source image in accordance with one or more embodiments described herein.
Figure 4:
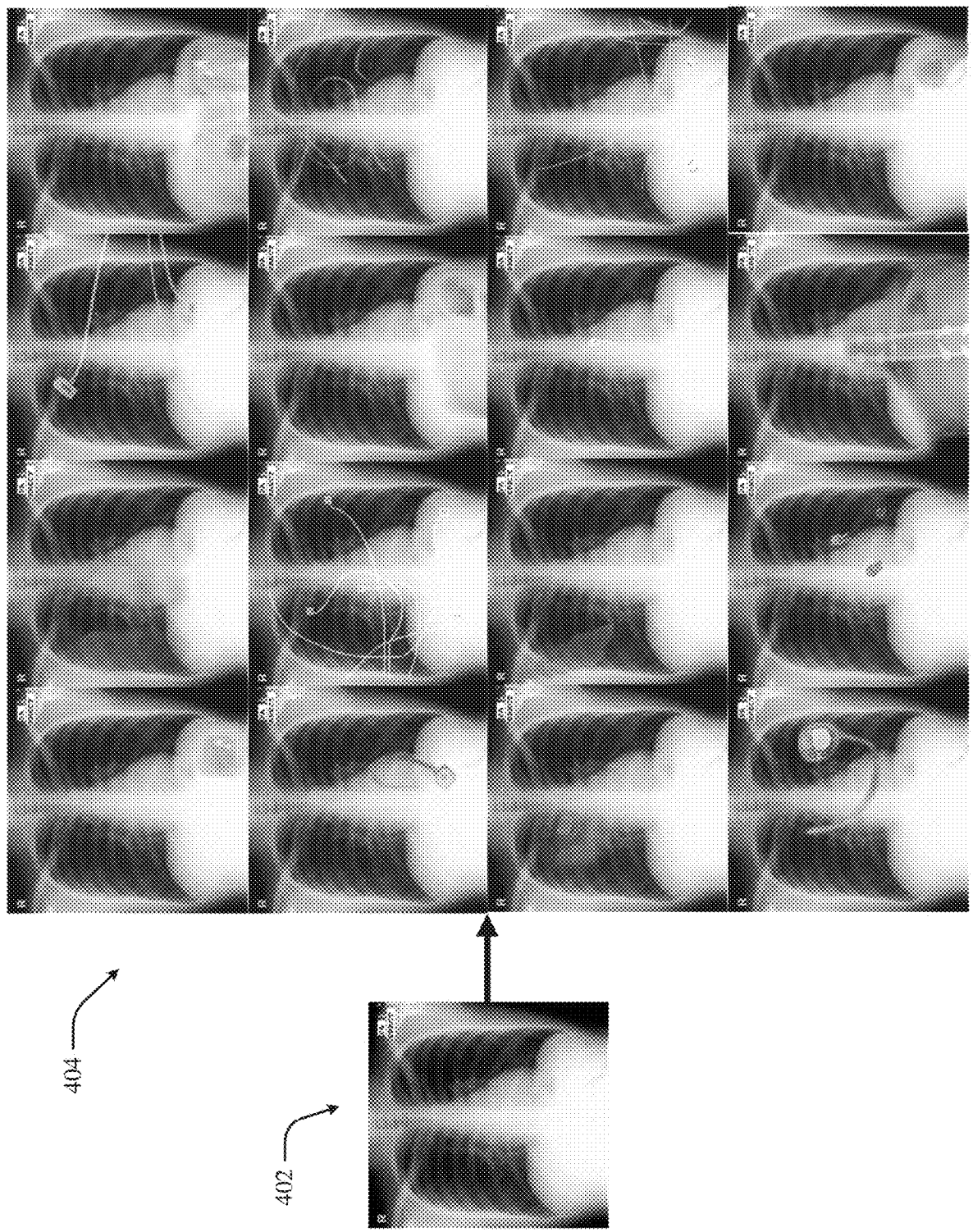

FIGS. 3-4 illustrate block diagrams of example, non-limiting preliminary training images 300 and 400 formed from an annotated source image in accordance with one or more embodiments described herein.

As shown in FIG. 3, the preliminary training images 204 can be generated from the annotated source image 104. In various cases, there can be N preliminary training images 204, for any suitable integer N. In other words, the element augmentation component 112 can create N electronic copies of the annotated source image 104, and can insert any suitable number and/or combinations/permutations of elements from the element catalog 202 into each of the N electronic copies of the annotated source image 104, thereby generating the N preliminary training images 204. As explained above, a goal of element insertion can be to increase the feature variety and/or diversity that is depicted in the annotated source image 104. Accordingly, the element augmentation component 112 can insert different numbers of different elements having different orientations and/or different dimensions into different locations of different copies of the annotated source image 104, thereby generating the preliminary training images 204. In other words, the single annotated source image 104 can be converted into the N preliminary training images 204.

As mentioned above, if a particular preliminary training image is formed by inserting only background elements or by inserting no elements at all, the annotation of the particular preliminary training image can be the same as the annotation of the annotated source image 104 (e.g., background elements can have no effect on the accuracy and/or completeness of an annotation). However, if a particular preliminary training image is formed by inserting any elements of interest, the annotation of the particular preliminary training image can be initialized as the the annotation of the annotated source image 104 and can be adjusted to reflect the inserted elements of interest. In this way, all of the preliminary training images 204 can have annotations based on the annotation of the annotated source image 104 and/or based on the inserted elements.

FIG. 4 depicts a real-world example showing how the annotated source image 104 can be used to create the preliminary training images 204. As shown, there can be an initial chest X-ray 402. In various cases, the initial chest X-ray 402 can be considered as the annotated source image 104. In various aspects, varied chest X-rays 404 can be generated by inserting various elements into the initial chest X-ray 402. Although FIG. 4 depicts sixteen varied chest X-rays 404 arranged in a four-by-four grid, this is exemplary and non-limiting. For ease of explanation, suppose that the top-most row is row 1 and the bottom-most row is row 4, and suppose that the left-most column is column 1 and the right-most column is column 4. As shown, the image at (row 1, column 1), the image at (row 1, column 4), the image at (row 2, column 3), and the image at (row 4, column 4) of the varied chest X-rays 404 can be formed by inserting and/or superimposing various features (e.g., stomach gas, intestinal growths/cists, colon cancers, digestive dyes, and/or so on) into and/or on the depicted abdominal cavity of the initial chest X-ray 402. As shown, the image at (row 1, column 3), the image at (row 2, column 1), the image at (row 2, column 2), the image at (row 2, column 4), the image at (row 3, column 4), and the image at (row 4, column 1) of the varied chest X-rays 404 can be formed by inserting and/or superimposing various features (e.g., intravenous tubing, breathing tubes, electrocardiogram wires/leads, pacemakers, and/or so on) into and/or on the depicted chest cavity of the initial chest X-ray 402. As shown, the image at (row 1, column 2), the image at (row 3, column 1), the image at (row 3, column 2), the image at (row 3, column 3), and the image at (row 4, column 2) of the varied chest X-rays 404 can be formed by inserting and/or superimposing various features (e.g., chest growths/nodules/masses, fluid-filled sacs, lacuna, consolidation, and/or so on) into and/or on the depicted chest cavity of the initial chest X-ray 402. Lastly, as shown, the image at (row 4, column 3) of the varied chest X-rays 404 can be formed by inserting and/or superimposing various features (e.g., metal screws, rods, and/or implants) into and/or on the initial chest X-ray 402.

Overall, different elements having different dimensions can be differently oriented in different locations of the initial chest X-ray 402 in order to create the varied chest X-rays 404.

Figure 5:
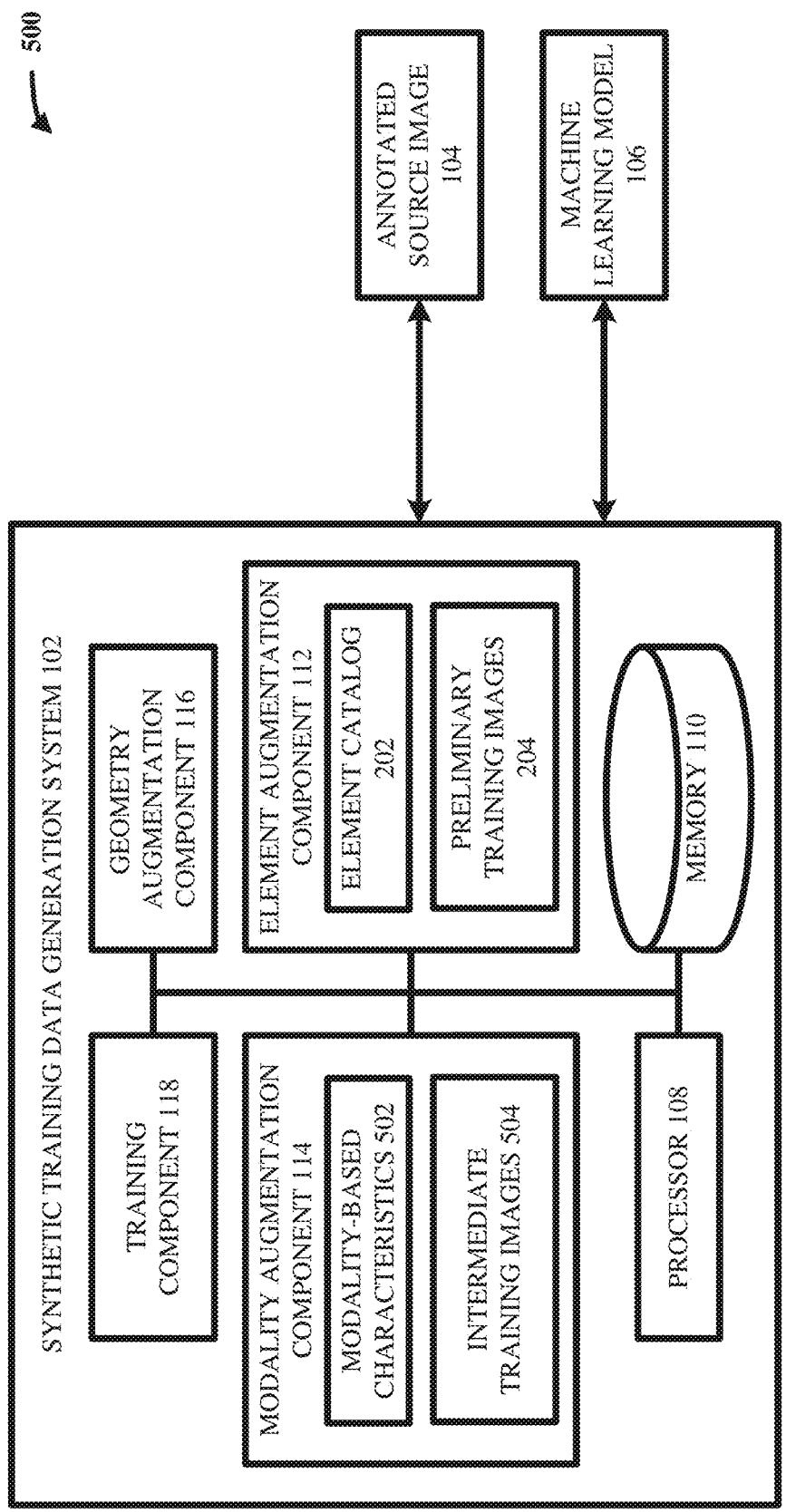
FIG. 5 illustrates a block diagram of an example, non-limiting system including modality-based characteristics that facilitates synthetic training data generation for improved machine learning model generalizability in accordance with one or more embodiments described herein.

FIG. 5 illustrates a block diagram of an example, non-limiting system 500 including modality-based characteristics that can facilitate synthetic training data generation for improved machine learning model generalizability in accordance with one or more embodiments described herein. As shown, the system 500 can, in some cases, comprise the same components as the system 200, and can further comprise modality-based characteristics 502 and intermediate training images 504.

In various aspects, the modality augmentation component 114 can comprise a list of modality-based characteristics 502 that are applicable to the preliminary training images 204. In various instances, the modality augmentation component 114 can vary, change, and/or modify any of the modality-based characteristics 502 of the preliminary training images 204 to generate intermediate training images 504. As mentioned above, the modality-based characteristics 502 can include any suitable image property that depends upon and/or is related to the image-capture device that generated the annotated source image 104. For example, the modality-based characteristics 502 can include gamma/radiation levels exhibited by and/or depicted in an image, brightness levels exhibited by and/or depicted in an image, contrast levels exhibited by and/or depicted in an image, blur levels exhibited by and/or depicted in an image, noise levels exhibited by and/or depicted in an image, texture exhibited by and/or depicted in an image, field of view exhibited by and/or depicted in an image, resolution exhibited by and/or depicted in an image, device artifacts (e.g., lens scratches, lens dust, lens glares) exhibited by and/or depicted in an image, and/or so on. In various aspects, the modality augmentation component 114 can generate the intermediate training images 504 by varying, changing, and/or modifying any of the modality-based characteristics 502 of the preliminary training images 204 (e.g., different electronic copies of each of the preliminary training images 204 can be made, and different modality-based characteristics (e.g., 502) of the different electronic copies can be differently varied to generate the intermediate training images 504).

In various instances, the list of modality-based characteristics 502 can be considered as a parametrization of the space of possible/potential image properties that depend upon the device modality that generated and/or captured the annotated source image 104. In other words, a space of possible/potential image properties which can vary from image-capture device modality to image-capture device modality can be conceived, and the list of modality-based characteristics 502 can be constructed and/or configured so as to span and/or substantially span that space. In various cases, such a parametrized space can depend upon the operational context of the machine learning model 106.

In various embodiments, the modality augmentation component 114 can update and/or change the list of modality-based characteristics 502 (e.g., can update and/or change the list of modifiable image characteristics/properties that are related to and/or associated with device modality and that are used to generate the intermediate training images 504). For instance, in some cases, the list of modality-based characteristics 502 can be initialized with an existing set of modifiable image characteristics/properties that are related to device modality. However, in various aspects, the modality augmentation component 114 can periodically and/or aperiodically query any suitable database and/or data structure which is accessible to the modality augmentation component 114 to check if new modifiable image characteristics/properties related to device modality are available (e.g., to check if image characteristics/properties that depend upon device modality and that are not currently flagged/marked as modifiable are known so that such new image characteristics/properties can be used to generate the intermediate training images 504). If it is determined that such new modifiable image characteristics/properties related to device modality are available, the modality augmentation component 114 can include such new image characteristics/properties in the list of modality-based characteristics 502 and can thus begin modifying such new image characteristics/properties when generating the intermediate training images 504. As another example, the modality augmentation component 114 can receive input from an operator, which input indicates a new image characteristic/property that is not already included in the list of modality-based characteristics 502. In various aspects, the modality augmentation component 114 can accordingly add the new image characteristic/property to the list of modality-based characteristics 502 and can thus begin modifying the new characteristic/property to generate the intermediate training images 504. In this way, the list of modality-based characteristics 502 can be updated, changed, amended, edited, and/or modified as desired so as to suit different operational contexts.

As an example, suppose that the list of modality-based characteristics 502 includes image gamma/radiation level, image brightness level, and image contrast level. Thus, the modality augmentation component 114 can modify and/or vary different combinations/permutations of gamma/radiation level, brightness level, and/or contrast level of the preliminary training images 204 in order to generate the intermediate training images 504. In various aspects, the modality augmentation component 114 can retrieve from any suitable database and/or data structure (and/or can receive as input from an operator) an indication that image blur level is now a modifiable image property that is related to device modality. Since the list of modality-based characteristics 502 does not already include image blur level, the modality augmentation component 114 can add image blur level to the list of modality-based characteristics 502. Thus, the modality augmentation component 114 can begin altering/modifying image blur level of the preliminary training images 204 in order to generate the intermediate training images 504. In this way, the list of modality-based characteristics 502 can be updated and/or enlarged over time and/or as desired.

Figure 6:
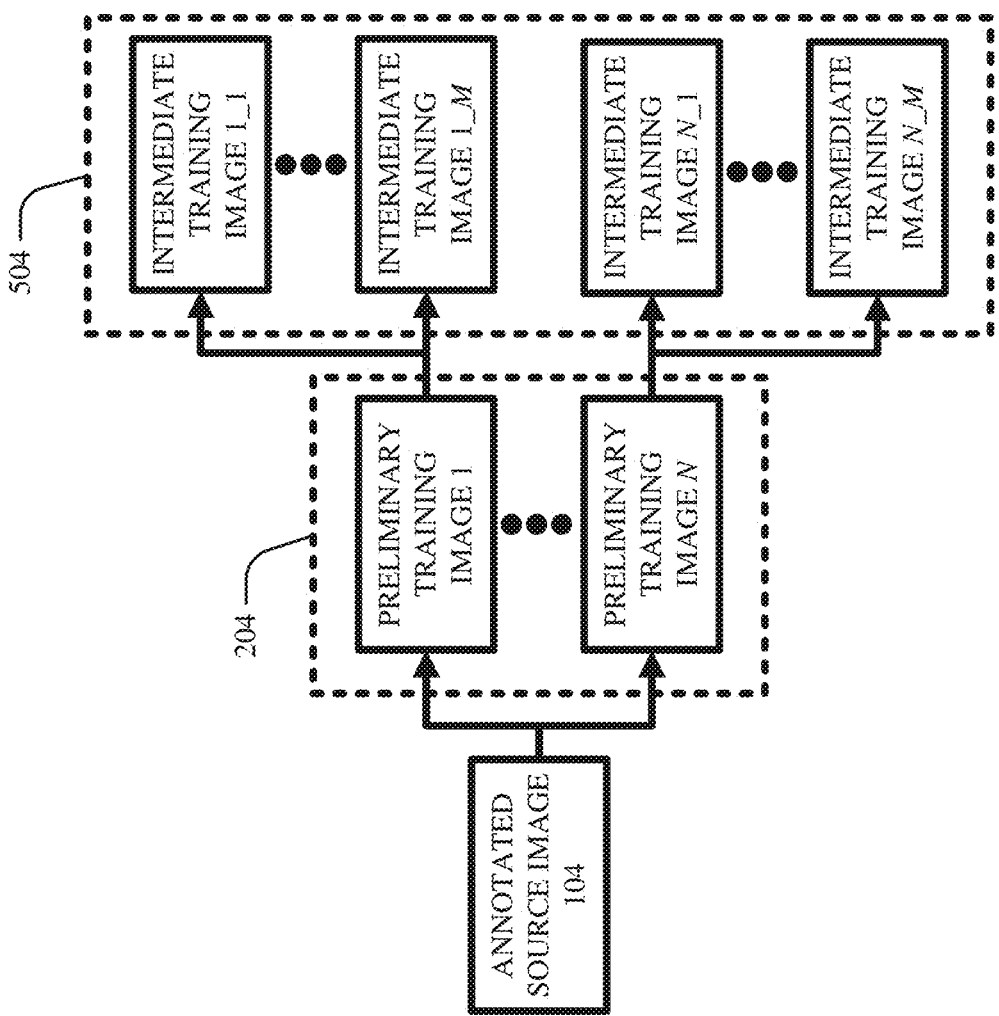
FIG. 6 illustrates a block diagram of example, non-limiting intermediate training images formed from preliminary training images in accordance with one or more embodiments described herein.

FIG. 6 illustrates a block diagram of example, non-limiting intermediate training images 600 formed from preliminary training images in accordance with one or more embodiments described herein.

As shown in FIG. 6, the intermediate training images 504 can be generated from the preliminary training images 204. In various cases, there can be M intermediate training images 504 for each of the preliminary training images 204, for any suitable integer M (e.g., intermediate training image 1_1 to intermediate training image 1_M formed from the preliminary training image 1; intermediate training image N_1 to intermediate training image N_M formed from the preliminary training image N, and/or so on). In other words, the modality augmentation component 114 can create M electronic copies of each of the N preliminary training images 204, and can vary, change, and/or modify any suitable number of modality-based characteristics (e.g., 502) of each of the M electronic copies of each of the N preliminary training images 204, thereby generating a total of N*M intermediate training images 504. As explained above, a goal of modality-based characteristic modification can be to increase the variety and/or diversity that is depicted in the preliminary training images 204. Accordingly, the modality augmentation component 114 can differently adjust different combinations/permutations of different modality-based characteristics of different copies of the preliminary training images 204, thereby generating the intermediate training images 504. In other words, the single annotated source image 104 can be converted into the N*M intermediate training images 504.

As mentioned above, modification of any of the modality-based characteristics 502 can have no effect on the accuracy and/or completeness of an annotation. Accordingly, a particular intermediate training image formed from a particular preliminary training image can have the same as annotation as the particular preliminary training image.

Figure 7:
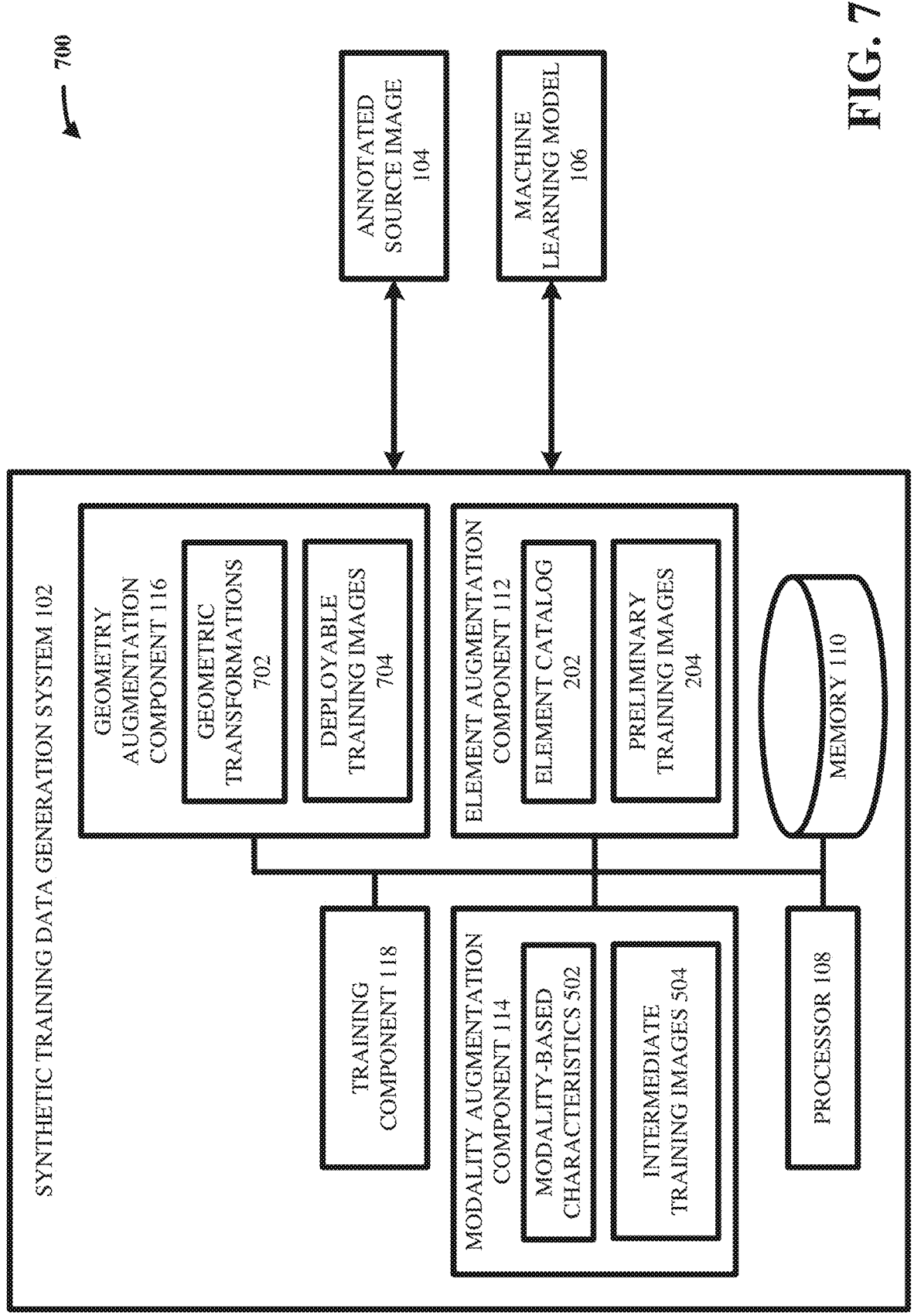
FIG. 7 illustrates a block diagram of an example, non-limiting system including geometric transformations that facilitates synthetic training data generation for improved machine learning model generalizability in accordance with one or more embodiments described herein.

FIG. 7 illustrates a block diagram of an example, non-limiting system 700 including geometric transformations that can facilitate synthetic training data generation for improved machine learning model generalizability in accordance with one or more embodiments described herein. As shown, the system 700 can, in various instances, comprise the same components as the system 500, and can further comprise geometric transformations 702 and deployable training images 704.

In various aspects, the geometry augmentation component 116 can comprise a list of geometric transformations 702 that are applicable to the intermediate training images 504. In various instances, the geometry augmentation component 116 can apply any of the geometric transformations 702 to the intermediate training images 504 to generate deployable training images 704. As mentioned above, the geometric transformations 702 can include any suitable mathematic transformation and/or operation that can spatially alter the depicted geometry of an image (e.g., of the intermediate training images 504). For example, the list of geometric transformations 702 can include reflecting an image about any suitable axis, rotating an image by any suitable magnitude about any suitable axis, panning an image in any suitable direction by any suitable magnitude, tilting an image in any suitable direction by any suitable magnitude, zooming in and/or out on any suitable portion of an image by any suitable magnitude, cropping any suitable portion of an image in any suitable way, expanding an image in any suitable direction and by any suitable magnitude, contracting an image in any suitable direction and by any suitable magnitude, distorting any suitable portion of an image in any suitable way and by any suitable magnitude, harmonizing and/or de-harmonizing an image in any suitable way and by any suitable magnitude, applying any suitable affine and/or elastic transformation to an image in any suitable way, and/or so on. In various aspects, the geometry augmentation component 116 can generate the deployable training images 704 by applying any of the geometric transformations 702 to the intermediate training images 504 (e.g., different electronic copies of each of the intermediate training images 504 can be made, and different geometric transformations (e.g., 702) of the different electronic copies can be applied to generate the deployable training images 704).

In various instances, the geometric transformations 702 can be considered as a parametrization of the space of possible/potential mathematical transformations that can be applied to an image. In other words, a space of possible/potential mathematical transformations and/or operations which can be applied to an image can be conceived, and the list of geometric transformations 702 can be constructed and/or configured so as to span and/or substantially span that space. In various cases, such a parametrized space can depend upon the operational context of the machine learning model 106.

In various embodiments, the geometry augmentation component 116 can update and/or change the list of geometric transformations 702 (e.g., can update and/or change the list of mathematical operations/transformations that are used to generate the deployable training images 704). For instance, in some cases, the list of geometric transformations 702 can be initialized with an existing set of mathematical operations/transformations that are appliable to images. However, in various aspects, the geometry augmentation component 116 can periodically and/or aperiodically query any suitable database and/or data structure which is accessible to the geometry augmentation component 116 to check if new mathematical operations/transformations appliable to images are available (e.g., to check if mathematical operations/transformations that are not currently flagged/marked as appliable to images are known so that such new mathematical operations/transformations can be used to generate the deployable training images 704). If it is determined that such new mathematical operations/transformations are available, the geometry augmentation component 116 can include such new mathematical operations/transformations in the list of geometric transformations 702 and can thus begin applying such new mathematical operations/transformations when generating the deployable training images 704. As another example, the geometry augmentation component 116 can receive input from an operator, which input indicates a new mathematical operation/transformation that is not already included in the list of geometric transformations 702. In various aspects, the geometry augmentation component 116 can accordingly add the new mathematical operation/transformation to the list of geometric transformations 702 and can thus begin applying the new mathematical operation/transformation to generate the deployable training images 704. In this way, the list of geometric transformations 702 can be updated, changed, amended, edited, and/or modified as desired so as to suit different operational contexts.

As an example, suppose that the list of geometric transformations 702 includes image rotating, image reflecting, and image tilting. Thus, the geometry augmentation component 116 can apply different combinations/permutations of image rotations, image reflections, and/or image tilts to the intermediate training images 504 in order to generate the deployable training images 704. In various aspects, the geometry augmentation component 116 can retrieve from any suitable database and/or data structure (and/or can receive as input from an operator) an indication that image distorting is now an available geometric transformation. Since the list of geometric transformations 702 does not already include image distorting, the geometry augmentation component 116 can add image distorting to the list of geometric transformations 702. Thus, the geometry augmentation component 116 can begin applying image distortion to the intermediate training images 504 in order to generate the deployable training images 704. In this way, the list of geometric transformations 702 can be updated and/or enlarged over time and/or as desired.

Figure 8:
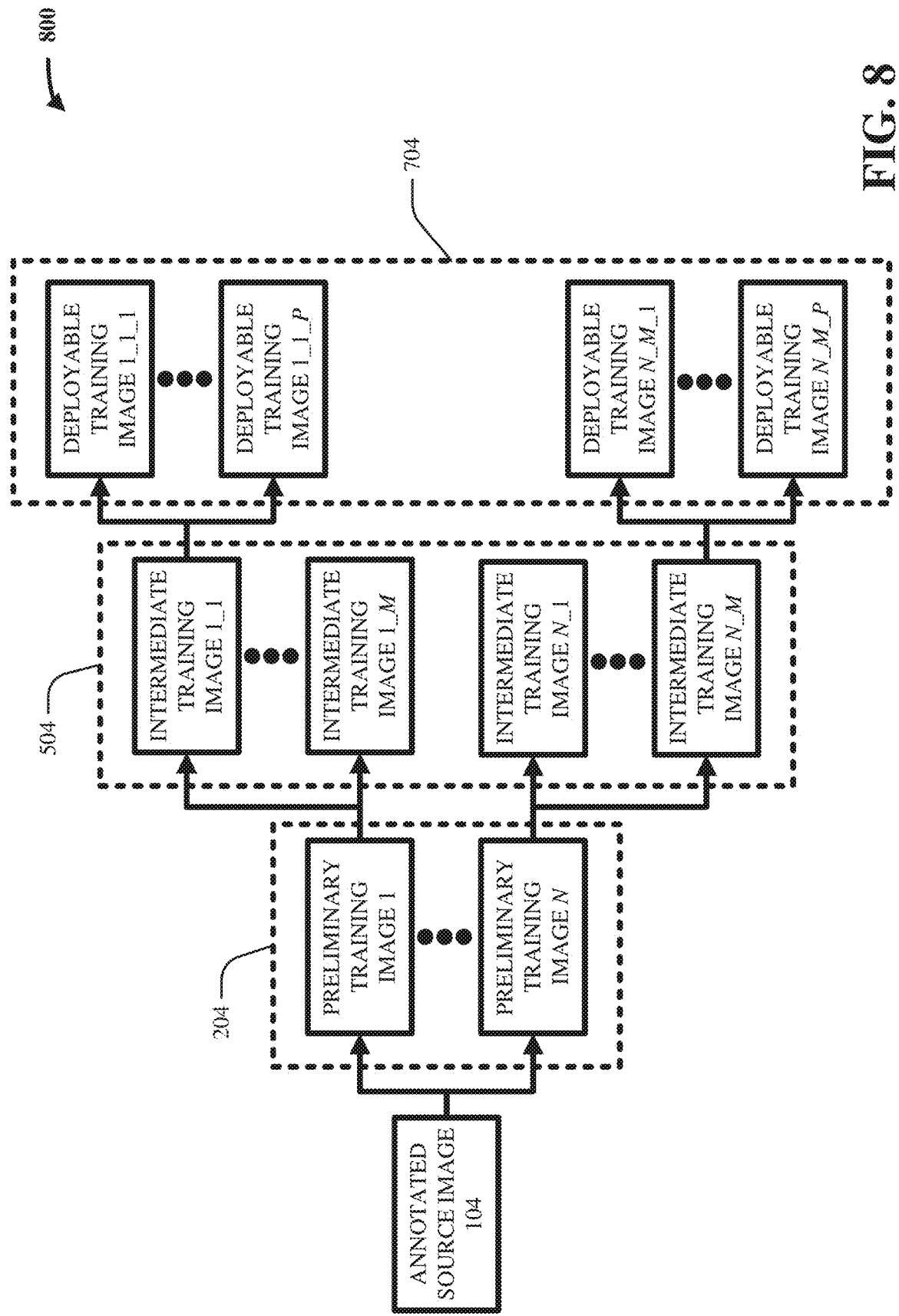
FIG. 8 illustrates a block diagram of example, non-limiting deployable training images formed from intermediate training images in accordance with one or more embodiments described herein.

FIG. 8 illustrates a block diagram of example, non-limiting deployable training images 800 formed from intermediate training images in accordance with one or more embodiments described herein.

As shown in FIG. 8, the deployable training images 704 can be generated from the intermediate training images 504. In various cases, there can be P deployable training images 704 for each of the intermediate training images 504, for any suitable integer P (e.g., deployable training image 1_1_1 to deployable training image 1_1_P formed from intermediate training image 1_1; deployable training image N_M_1 to deployable training image N_M_P formed from intermediate training image N_M; and/or so on). In other words, the geometry augmentation component 116 can create P electronic copies of each of the N*M intermediate training images 504, and can apply any suitable number of geometric transformations (e.g., 702) to each of the P electronic copies of each of the N*M intermediate training images 504, thereby generating a total of N*M*P deployable training images 704. As explained above, a goal of geometric transformation can be to increase the variety and/or diversity that is depicted in the intermediate training images 504. Accordingly, the geometry augmentation component 116 can apply different combinations/permutations of different geometric transformations to different copies of the intermediate training images 504, thereby generating the deployable training images 704. In other words, the single annotated source image 104 can be converted into the N*M*P deployable training images 704.

As mentioned above, application of any of the geometric transformations 702 can have no effect on the accuracy and/or completeness of an annotation. Accordingly, a particular deployable training image formed from a particular intermediate training image can have the same annotation as the particular intermediate training image.

As shown, in various aspects, the number of deployable training images 704 can be greater than the number of intermediate training images 504, which can be greater than the number of preliminary training images 204.

Figure 9:
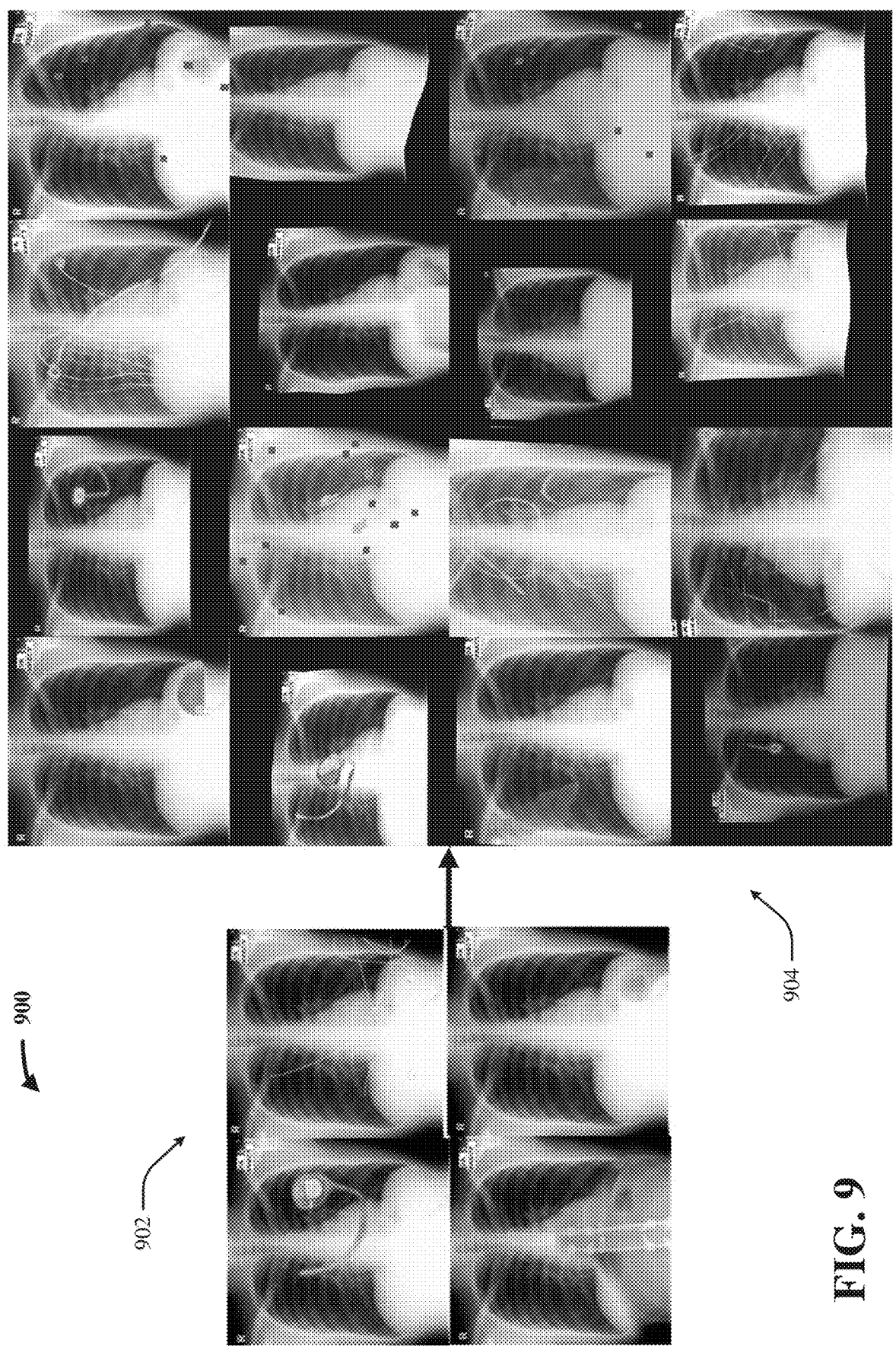
FIG. 9 illustrates a block diagram of example, non-limiting variations of modality-based characteristics and geometric characteristics in accordance with one or more embodiments described herein.

FIG. 9 illustrates a block diagram of example, non-limiting variations of modality-based characteristics and/or geometric characteristics in accordance with one or more embodiments described herein.

In other words, FIG. 9 depicts a real-world example showing how the preliminary training images 204 can be used to create the intermediate training images 504 and/or the deployable training images 704. As shown, there can be augmented X-rays 902. In various cases, modality-based characteristics of the augmented X-rays 902 and/or geometric characteristics of the augmented X-rays 902 can be manipulated and/or modified as described above to create the further-augmented X-rays 904. Although FIG. 9 depicts sixteen further-augmented X-rays 904 arranged in a four-by-four grid, this is exemplary and non-limiting. For ease of explanation, suppose that the top-most row is row 1 and the bottom-most row is row 4, and suppose that the left-most column is column 1 and the right-most column is column 4. As shown, the image at (row 1, column 3), the image at (row 2, column 2), the image at (row 3, column 2), the image at (row 4, column 1), and the image at (row 4, column 3) of the further augmented X-rays 904 can be formed by increasing and/or decreasing brightness/contrast/gamma levels of the augmented X-rays 902. As shown, the image at (row 1, column 2), the image at (row 2, column 1), the image at (row 2, column 3), the image at (row 2, column 4), the image at (row 3, column 2), the image at (row 3, column 3), the image a (row 4, column 1), the image at (row 4, column 2), the image at (row 4, column 3), and the image at (row 4, column 4) of the further-augmented X-rays 904 can be formed by cropping, zooming, and/or optically distorting the augmented X-rays 902. In various cases, any other suitable transformations and/or modifications are possible.

In various aspects, as mentioned above, the training component 218 can train the machine learning model 106 on the deployable training images 704.

Figure 10:
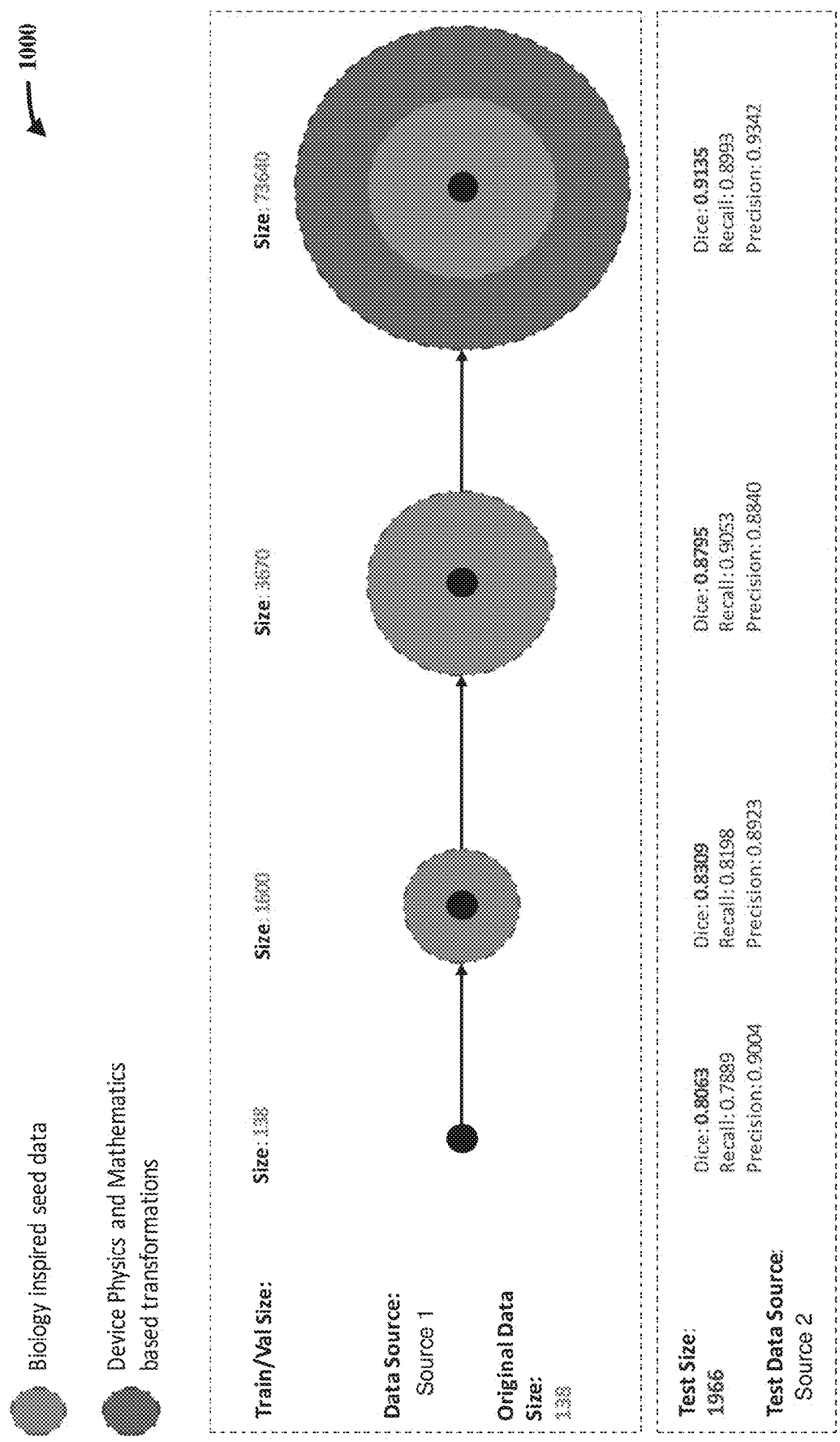
FIG. 10 illustrates example, non-limiting experimental results in accordance with one or more embodiments described herein.

FIG. 10 illustrates example, non-limiting experimental results 1000 in accordance with one or more embodiments described herein.

In various aspects, the inventors of various embodiments of the subject innovation generated training data sets as described herein (e.g., via element/feature insertion, via modality-based characteristic modification, via geometric transformation), and their experiments revealed that a lung-segmentation machine learning model (e.g., 106) trained on the generated training data sets exhibited significantly improved performance/efficacy as compared to being trained on a conventional training data set. Specifically, as shown in FIG. 10, four different trials were conducted in which it was desired to train the lung-segmentation machine learning model on an original data set of size 138 (e.g., 138 training images in the original data set). A first trial was performed in which the machine learning model was trained only on the original data set. A second trial was performed in which element/feature insertion was performed to a limited extent (e.g., denoted by the small green annular ring). In this second trial, the element/feature insertion caused the original data set to grow from a size of 138 to a size of 1600 (e.g., after element/feature insertion, the data set included 1600 training images). A third trial was performed in which element/feature insertion was performed to a greater extent (e.g., denoted by the large green annular ring). In this third trial, the element/feature insertion caused the original data set to grow from a size of 138 to a size of 3670. Lastly, a fourth trial was performed in which element/feature insertion was performed to the greater extent and in which modality-based characteristics were varied and geometric transformations were applied (e.g., denoted by the blue annular ring). In this fourth trial, the element/feature insertion, the modality-based characteristic variation, and the geometric transformations caused the original data set to grow from a size of 138 to a size of 73,640.

Various performance metrics of the trained machine learning model for each of these four trials are depicted in FIG. 10. The inventors used a test data set of size 1966 to test the performance/efficacy of the trained machine learning model in each trial. As shown, in the first trial (e.g., trained only on the original data size), the machine learning model achieved a Dice score of 0.8063; in the second trial (e.g., element insertion implemented to a limited degree), the machine learning model achieved a Dice score of 0.8309; in the third trial (e.g., element insertion implemented to a greater degree), the machine learning model achieved a Dice score of 0.8795; and in the fourth trial (e.g., element insertion implemented to a greater degree and modality-based modifications and geometric transformations implemented), the machine learning model achieve a Dice score of 0.9135. In other words, the machine learning model experienced significant performance/efficacy improvements when trained on data sets generated by various embodiments of the subject innovation (e.g., the machine learning model became more generalizable/robust, became more able to handle difficult and/or unseen test cases and/or so on). That is, as shown by FIG. 10, the herein-described techniques for increasing data set variability (e.g., element/feature insertion, modality-based variation, geometric transformations) can independently and/or collectively improve model performance. For at least these reasons, various embodiments of the subject innovation constitute a concrete and tangible technical improvement (e.g., they can improve the computational performance of machine learning models).

FIGS. 11-20 illustrate block diagrams of example, non-limiting image augmentations in accordance with one or more embodiments described herein. In other words, FIGS. 11-20 depicts real-world examples of various element insertions, various modality-based variations, and/or various geometric transformations that can be implemented in accordance with various embodiments.

Figure 11:
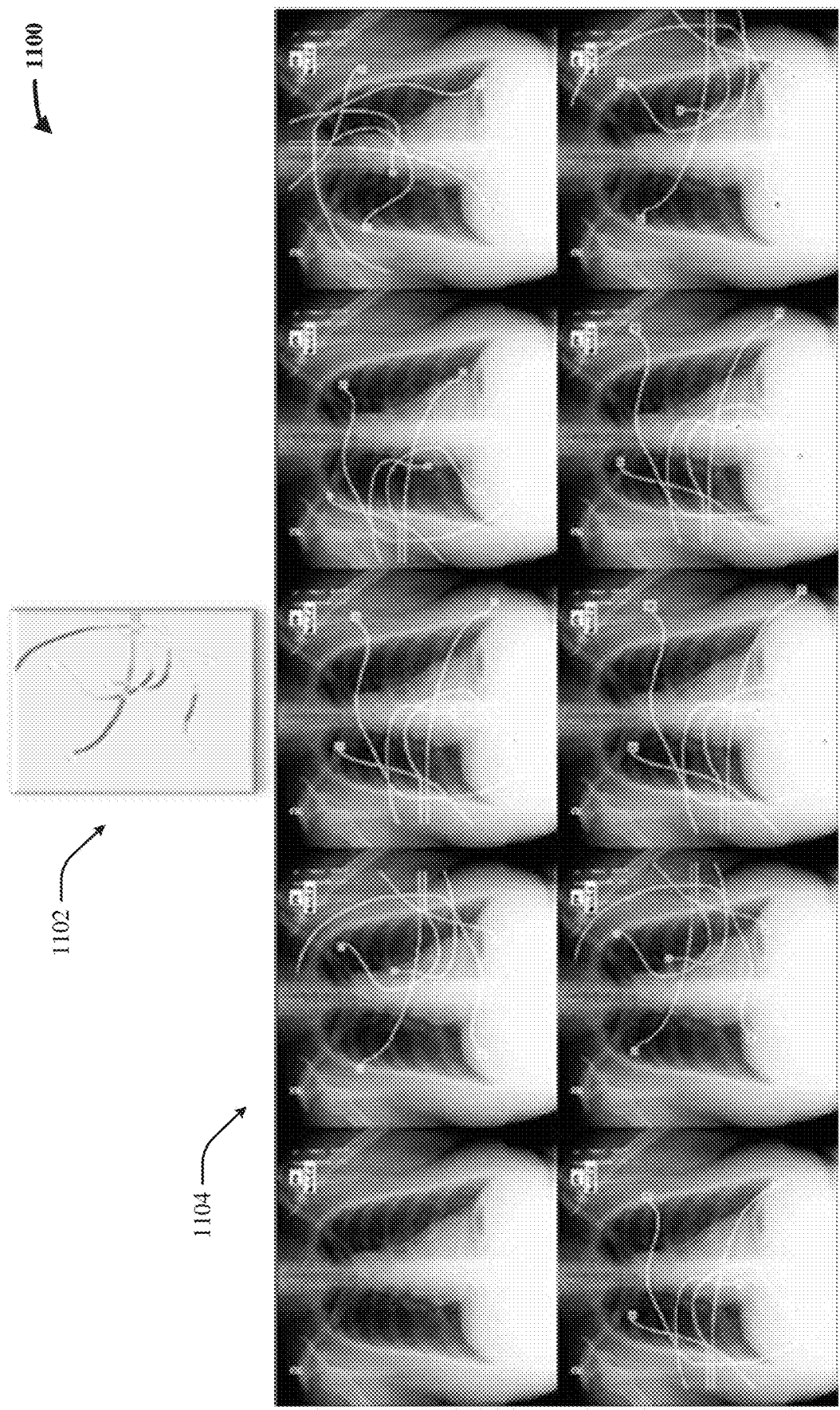
FIGS. 11-20 illustrate block diagrams of example, non-limiting image augmentations in accordance with one or more embodiments described herein.

FIG. 11 depicts wires/cables 1102 (e.g., electrocardiogram leads, intravenous tubing, breathing tubes, and/or so on) and depicts how the wires/cables 1102 can be inserted into and/or superimposed on various X-ray images 1104 in different locations, with different orientations, with different dimensions, with different thicknesses/intensities, with different shapes, and/or so on.

Figure 12:
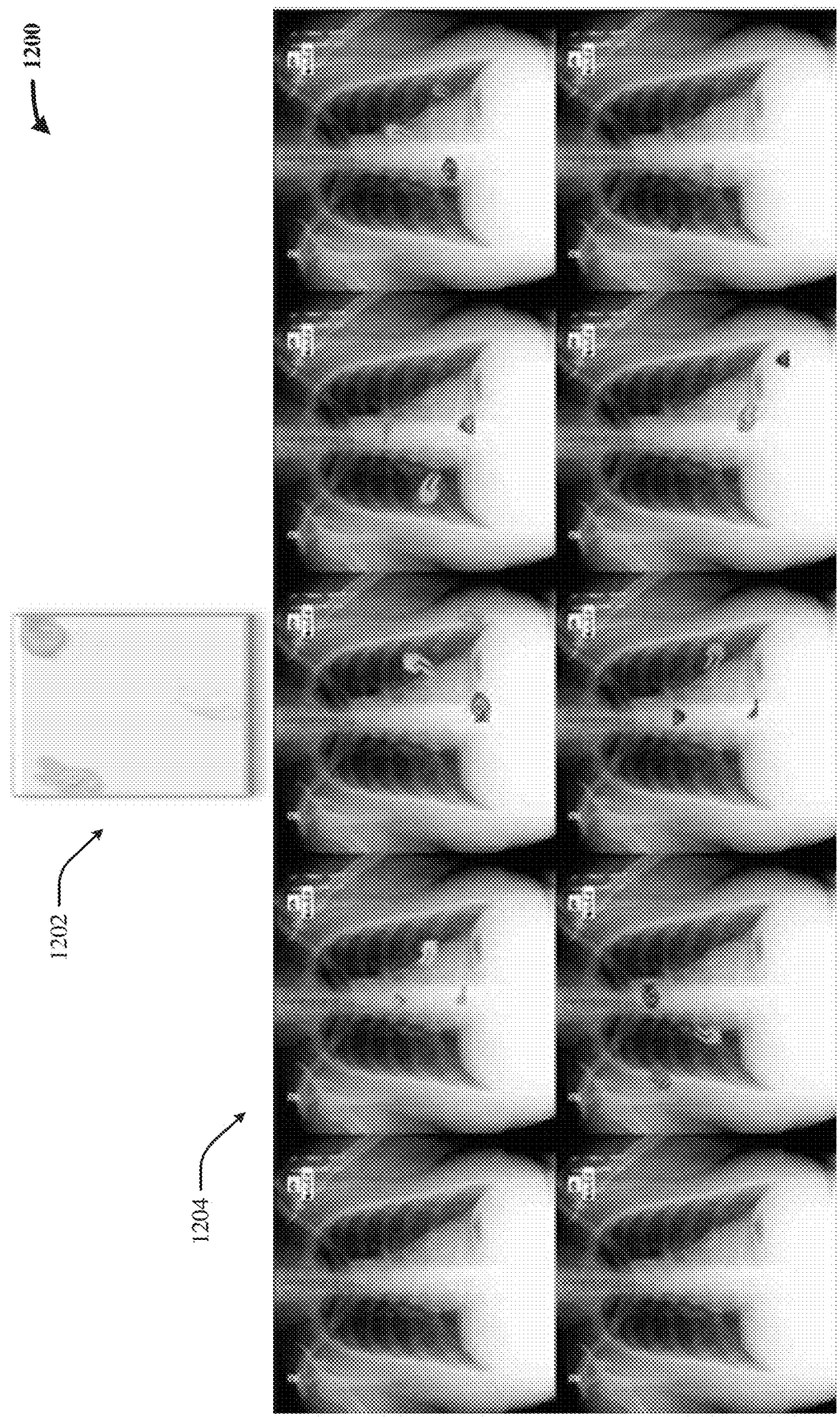

FIG. 12 depicts masses 1202 (e.g., fluid-filled sacs, growths, cists, and/or so on) and depicts how the masses 1202 can be inserted into and/or superimposed on various X-ray images 1204 in different locations, with different orientations, with different dimensions, with different thicknesses/intensities, with different shapes, and/or so on.

Figure 13:
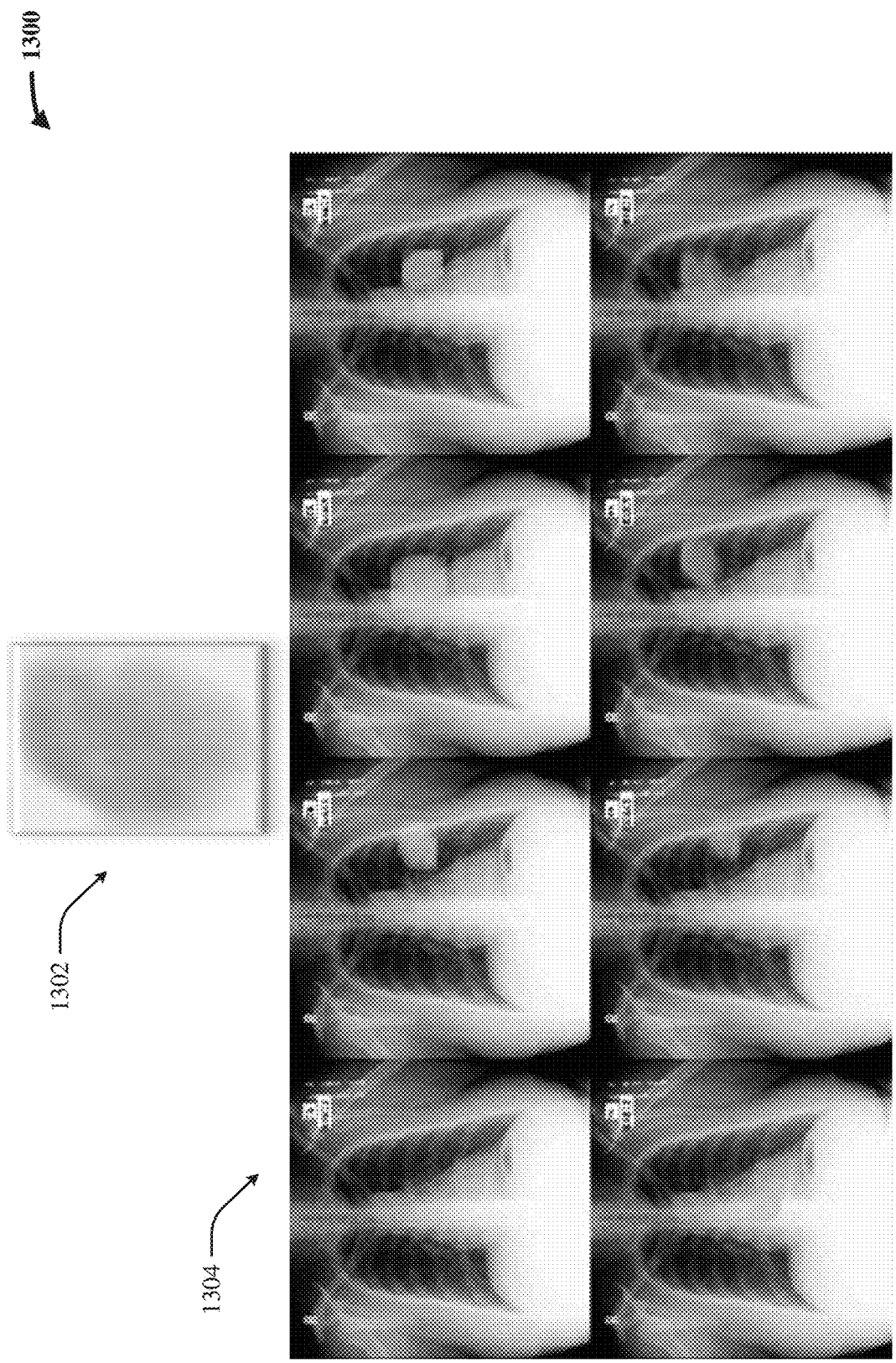

FIG. 13 depicts mass 1302 (e.g., tumor, and/or so on) and depicts how the mass 1302 can be inserted into and/or superimposed on various X-ray images 1304 in different locations, with different orientations, with different dimensions, with different thicknesses/intensities, with different shapes, and/or so on.

Figure 14:
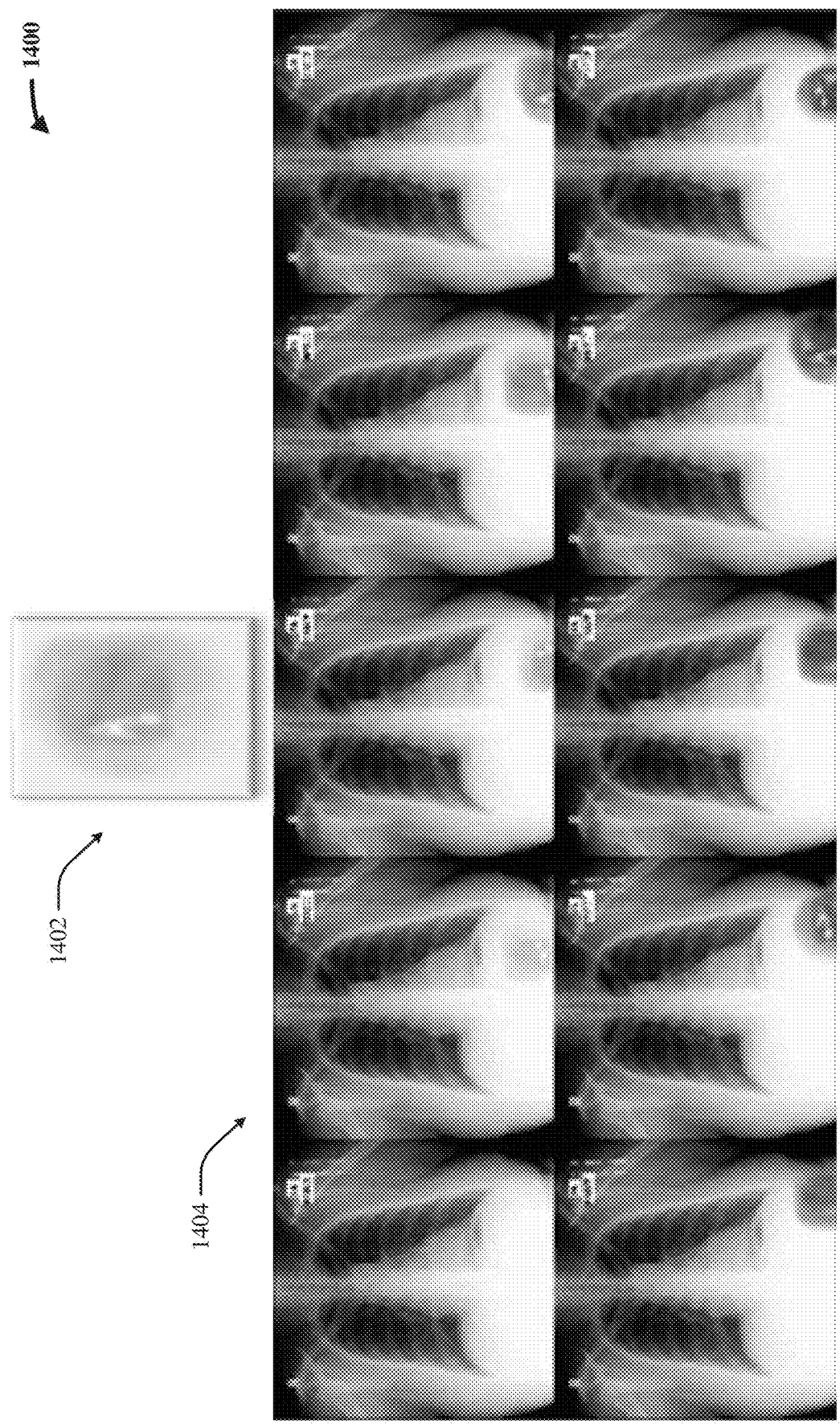

FIG. 14 depicts stomach gas 1402 and depicts how the stomach gas 1402 can be inserted into and/or superimposed on various X-ray images 1404 in different locations, with different orientations, with different dimensions, with different thicknesses/intensities, with different shapes, and/or so on. As explained above, note how the stomach gas 1402 can be inserted into abdominal regions of the various X-ray images 1404 rather than in chest regions of the various X-ray images 1404 (e.g., stomach gas cannot form in the chest, but can form in the abdomen).

Figure 15:

FIG. 15 depicts various X-ray images 1500 in which a gamma/radiation level is continuously varied. As shown, the gamma/radiation level is highest in the upper-left X-ray images and is lowest in the lower-right X-ray images.

Figure 16:
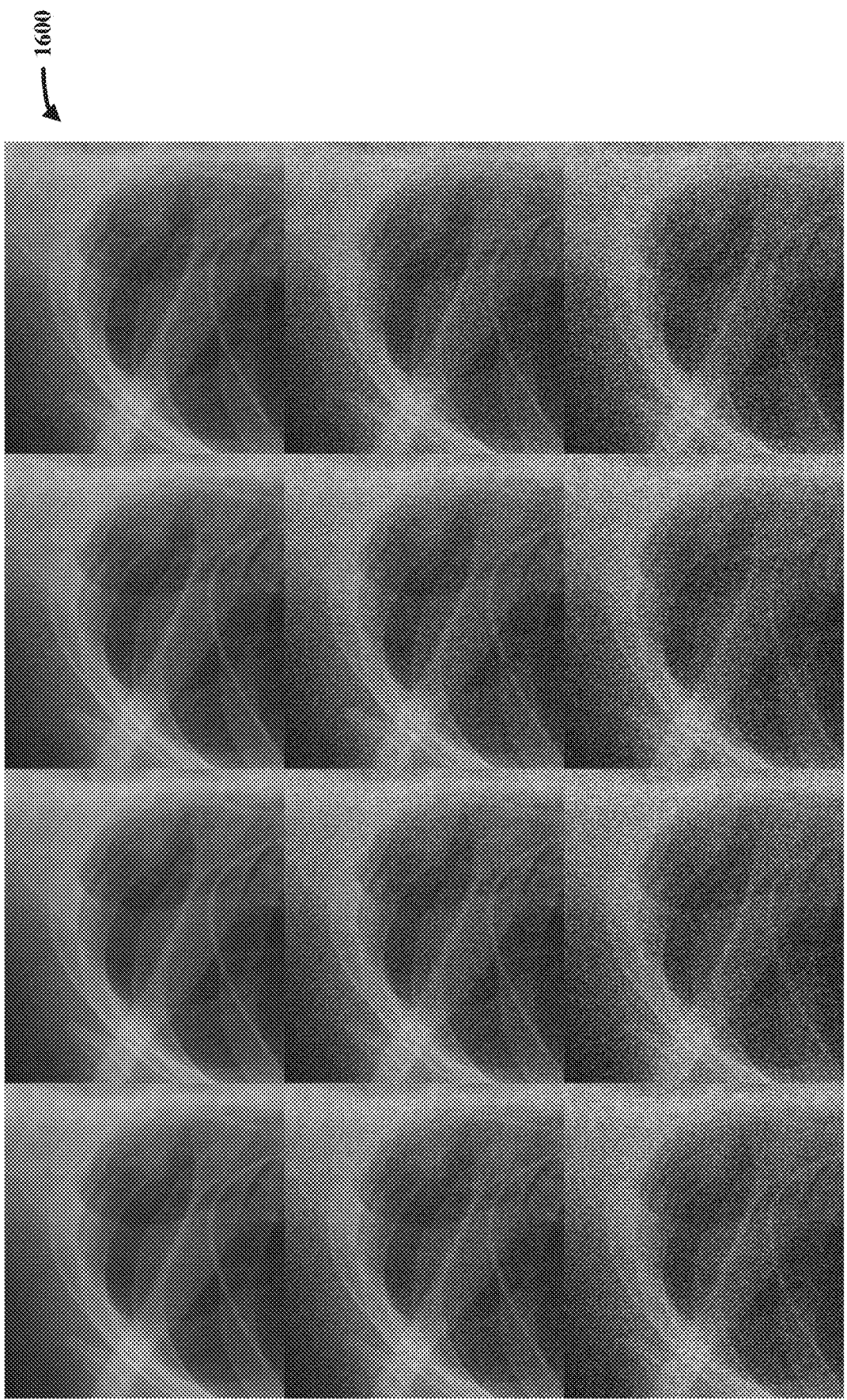

FIG. 16 depicts various X-ray images 1600 in which a Gaussian noise level is continuously varied. As shown, the Gaussian noise level is lowest in the upper-left X-ray images and is highest in the lower-right X-ray images.

Figure 17:
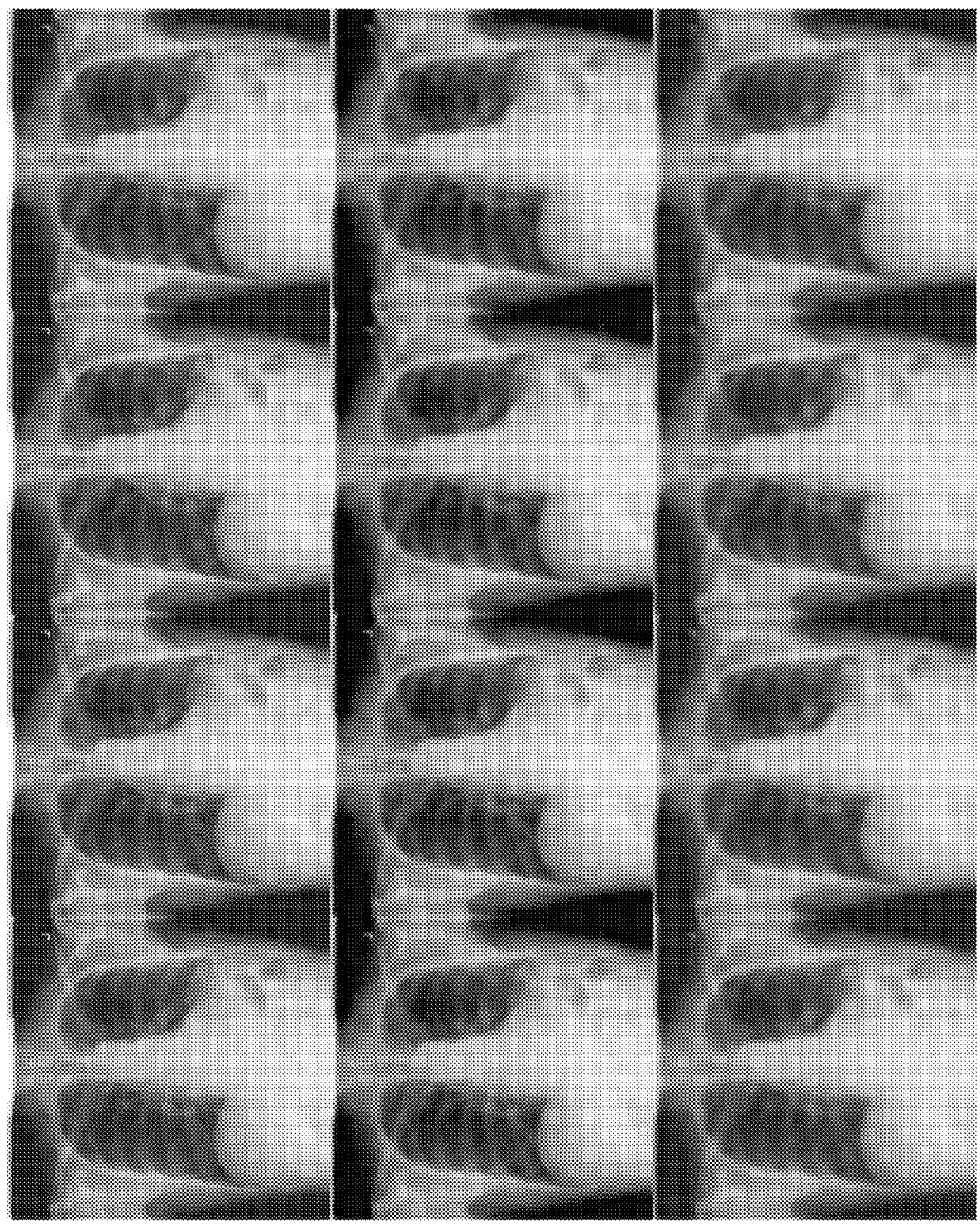

FIG. 17 depicts various X-ray images 1700 in which a Gaussian blur level is continuously varied. As shown, the Gaussian blur level is lowest in the upper-left X-ray images and is highest in the lower-right X-ray images.

Figure 18:
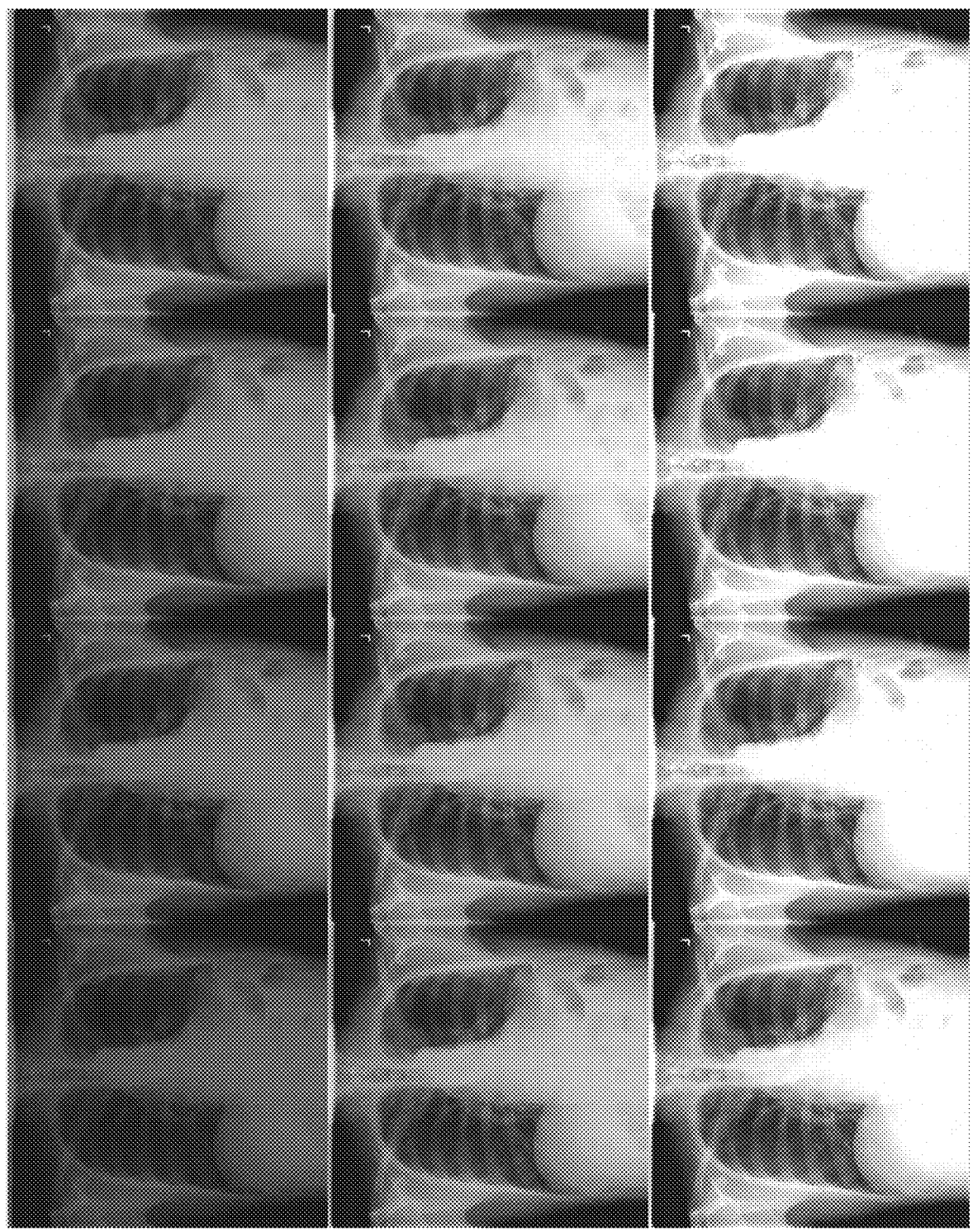

FIG. 18 depicts various X-ray images 1800 in which a contrast level is continuously varied. As shown, the contrast level is lowest in the upper-left X-ray images and is highest in the lower-right X-ray images.

Figure 19:
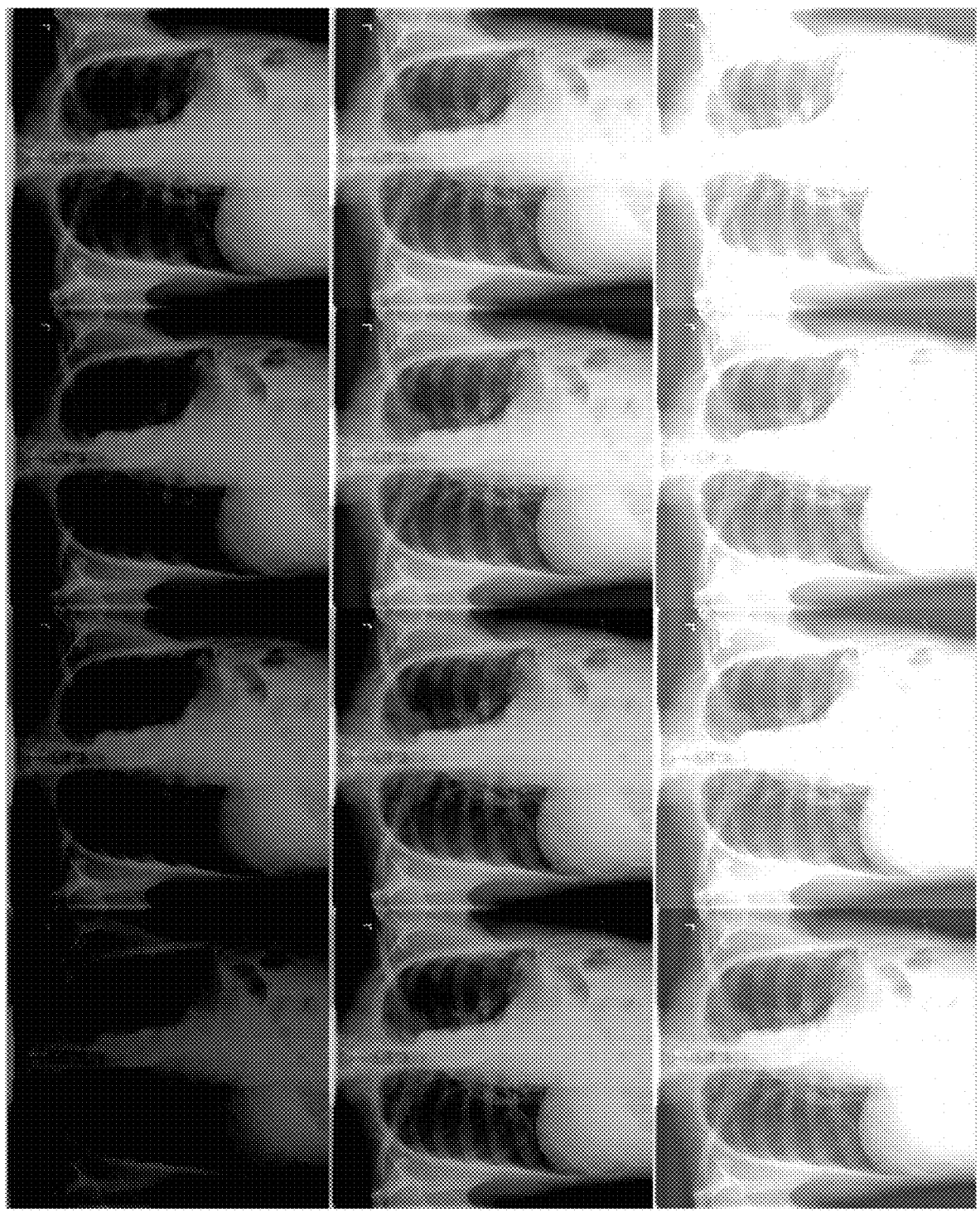

FIG. 19 depicts various X-ray images 1900 in which a brightness level is continuously varied. As shown, the brightness level is lowest in the upper-left X-ray images and is highest in the lower-right X-ray images.

Figure 20:
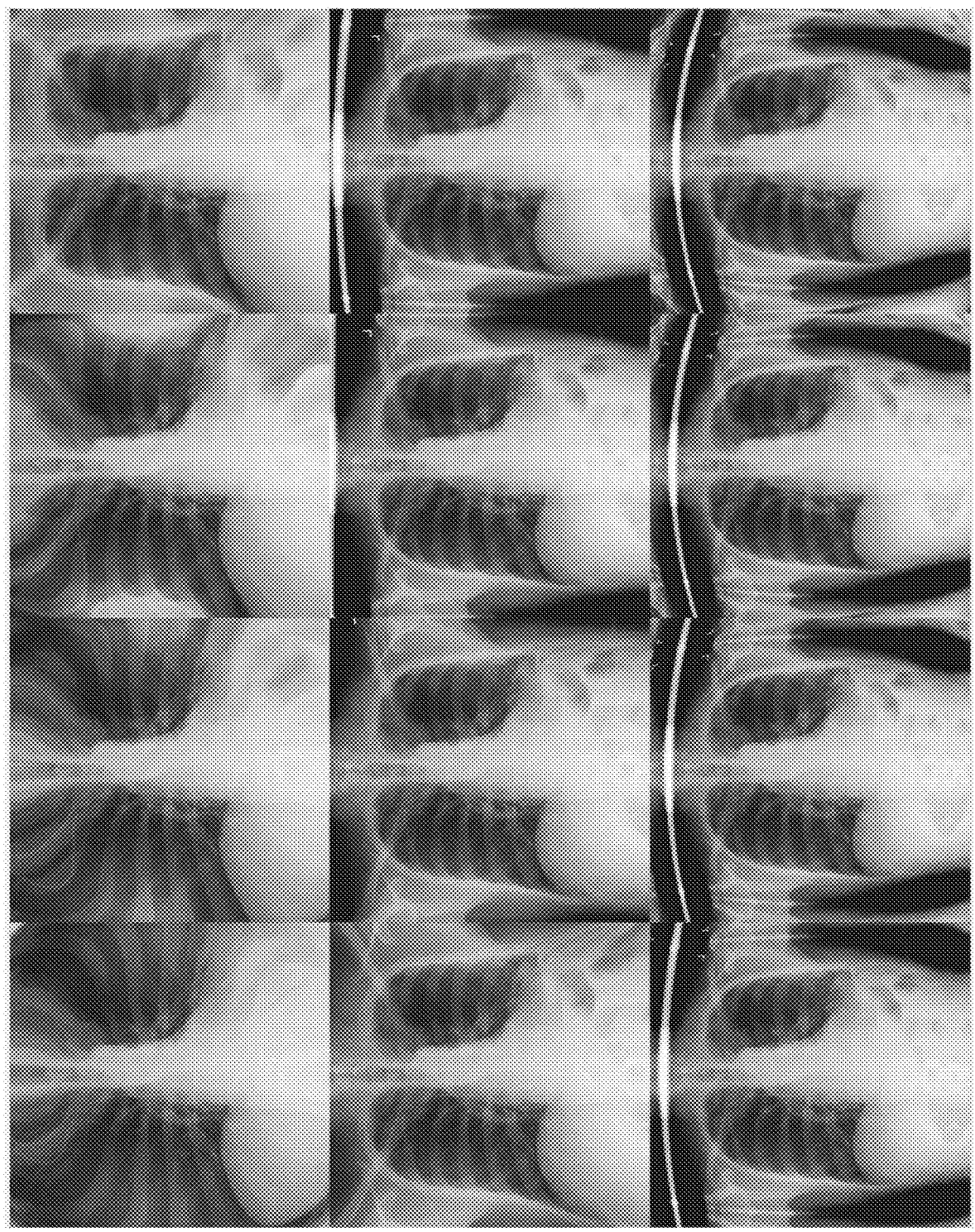

FIG. 20 depicts various X-ray images 2000 in which an exemplary optical distortion is continuously varied. As shown, the optical distortion is most readily apparent in the upper-left and lower-right X-ray images.

It should be appreciated that the augmentations illustrated in FIGS. 11-20 are exemplary and non-limiting. Any other suitable augmentations can be implemented in various embodiments.

Figure 21:
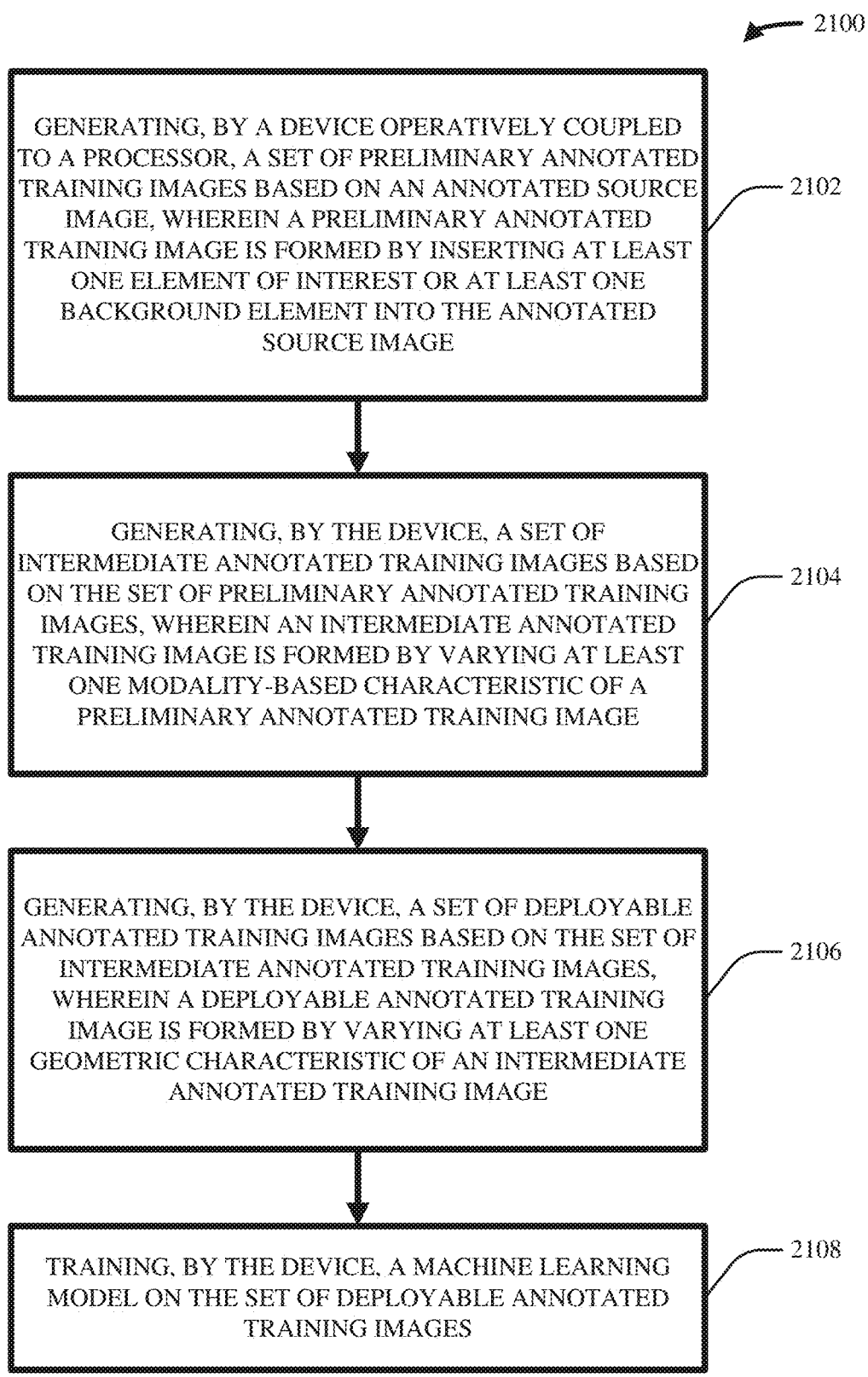
FIG. 21 illustrates a flow diagram of an example, non-limiting computer-implemented method that facilitates synthetic training data generation for improved machine learning model generalizability in accordance with one or more embodiments described herein.

FIG. 21 illustrates a flow diagram of an example, non-limiting computer-implemented method 2100 that can facilitate synthetic training data generation for improved machine learning model generalizability in accordance with one or more embodiments described herein.

In various embodiments, act 2102 can include generating, by a device operatively coupled to a processor (e.g., 112), a set of preliminary annotated training images (e.g., 204) based on an annotated source image (e.g., 104). In various aspects, a preliminary annotated training image can be formed by inserting at least one element of interest or at least one background element (e.g., from 202) into the annotated source image.

In various instances, act 2104 can include generating, by the device (e.g., 114), a set of intermediate annotated training images (e.g., 504) based on the set of preliminary annotated training images. In various cases, an intermediate annotated training image can be formed by varying at least one modality-based characteristic (e.g., from 502) of a preliminary annotated training image.

In various aspects, act 2106 can include generating, by the device (e.g., 116), a set of deployable annotated training images (e.g., 704) based on the set of intermediate annotated training images. In various instances, a deployable annotated training image can be formed by varying at least one geometric characteristic (e.g., by applying any of 702) of an intermediate annotated training image.

In various cases, act 2108 can include training, by the device (e.g., 118), a machine learning model (e.g., 106) on the set of deployable annotated training images.

Figure 22:
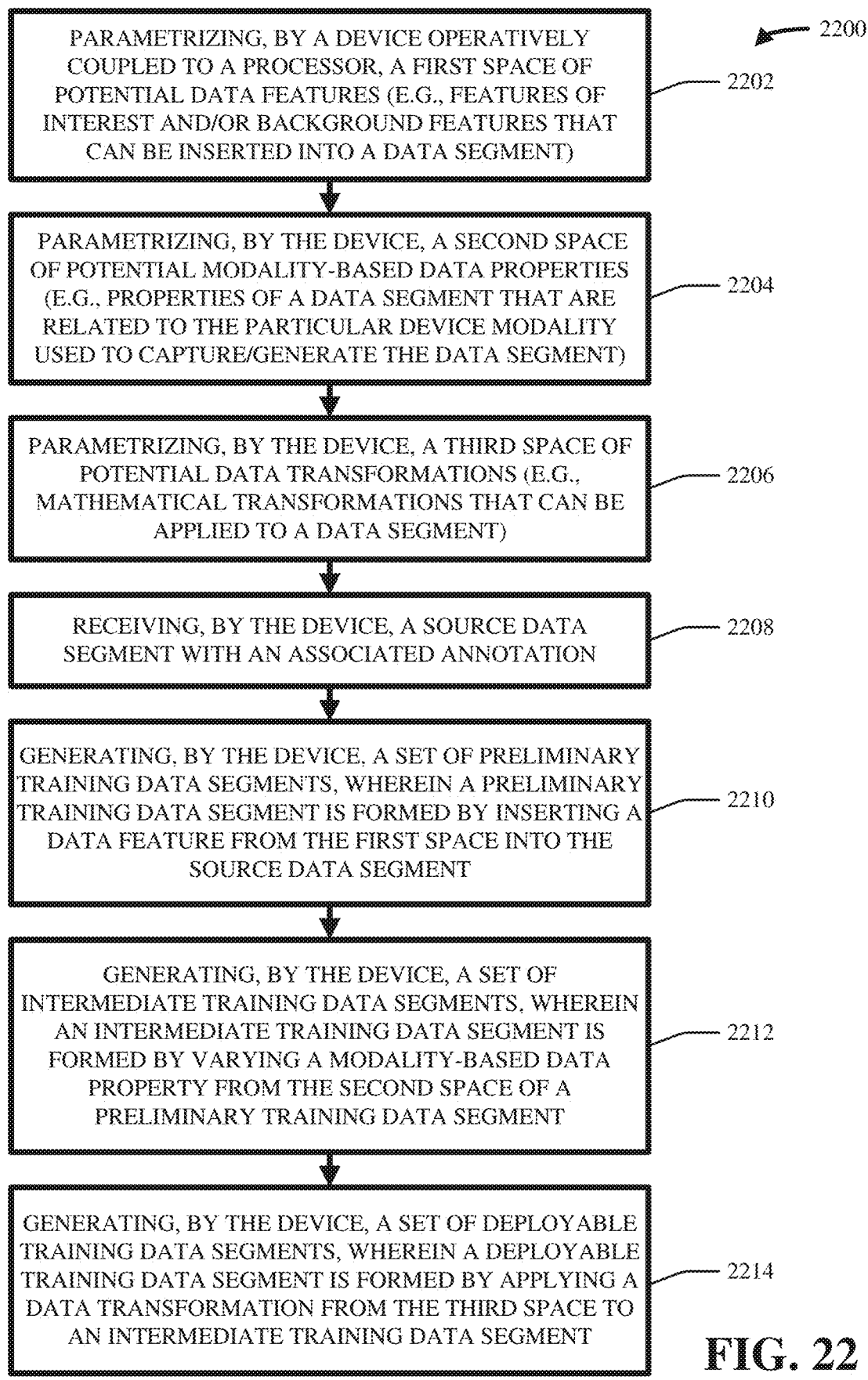
FIG. 22 illustrates a flow diagram of an example, non-limiting computer-implemented method that facilitates synthetic training data generation for improved machine learning model generalizability in accordance with one or more embodiments described herein.

FIG. 22 illustrates a flow diagram of an example, non-limiting computer-implemented method 2200 that can facilitate synthetic training data generation for improved machine learning model generalizability in accordance with one or more embodiments described herein.

As explained above, the herein teachings regarding how to synthetically increase training data variability are described, for ease of explanation, with respect to an imaging context (e.g., the machine learning model 106 is configured to analyze one or more images). However, in various aspects, the described teachings can be applied in any suitable context that utilizes machine learning models (e.g., models that analyze images, models that analyze sound recordings, and/or models that analyze any other suitable type of data). In such cases, it should be understood that the format of the source data (e.g., 104), the preliminary training data (e.g., 204), the intermediate training data (e.g., 504), the deployable training data (e.g., 704), the element catalog 202, the modality-based characteristics 502, and/or the geometric transformations 702 can depend upon the operational context (e.g., source/training images can be implemented if the machine learning model 106 is configured to analyze images; source/training sound recordings can be implemented if the machine learning model 106 is configured to analyze sound recordings; the types and/or format of insertable elements, modifiable modality-based characteristics, and/or mathematical transformations can depend on the format of the data which the machine learning model 106 is configured to analyze; and/or so on). The computer-implemented method 2200 demonstrates this generalizability.

In various embodiments, act 2202 can include parametrizing, by a device operatively coupled to a processor (e.g., 112), a first space of potential data features (e.g., 202). In various cases, these can include features of interest and/or background features that can be inserted into a data segment.

In various instances, act 2204 can include parametrizing, by the device (e.g., 114), a second space of potential modality-based data properties (e.g., 502). In various cases, these can include properties of a data segment that are related to the particular device modality that was used to capture and/or generate the data segment.

In various aspects, act 2206 can include parametrizing, by the device (e.g., 116), a third space of potential data transformations (e.g., 702). In various cases, these can include mathematical transformations and/or operations that can be applied to a data segment.

In various embodiments, act 2208 can include receiving, by the device, a source data segment (e.g., 104) with an associated annotation.

In various instances, act 2210 can include generating, by the device (e.g., 112), a set of preliminary training data segments (e.g., 204), wherein a preliminary training data segment can be formed by inserting a data feature from the first space (e.g., 202) into the source data segment. In various cases, this can include taking a first parametric sampling of values/states from the first space, and applying different combinations/permutations of the first parametric sampling to the source data segment to generate the set of preliminary training data segments.

In various aspects, act 2212 can include generating, by the device (e.g., 114), a set of intermediate training data segments (e.g., 504), wherein an intermediate training data segment can be formed by varying a modality-based data property from the second space (e.g., 502) of a preliminary training data segment. In various cases, this can include taking a second parametric sampling of values/states from the second space, and applying different combinations/permutations of the second parametric sampling to the set of preliminary training data segments to generate the set of intermediate training data segments.

In various embodiments, act 2214 can include generating, by the device (e.g., 116), a set of deployable training data segments (e.g., 704), wherein a deployable training data segment can be formed by applying a data transformation from the third space (e.g., 702) to an intermediate training data segment. In various cases, this can include taking a third parametric sampling of values/states from the third space, and applying different combinations/permutations of the third parametric sampling to the set of intermediate training data segments to generate the set of deployable training data segments.

In various cases, a machine learning model can then be trained on the det of deployable training data segments.

Various embodiments of the subject innovation can achieve their technical benefits by parametrizing a simulation space. Specifically, in various embodiments, it can be desired to train a machine learning model on a source data segment. In various aspects, a simulation space can be defined, where the simulation space can be considered as the domain of possible input data that can be fed to the machine learning model to be trained (e.g., for a machine learning model that is designed to analyze chest X-ray images, the simulation space can be the space of all possible chest X-ray images having different anatomical structures/features, different brightness/contrast levels, different distortion levels, different orientations/angles, and/or otherwise different image signatures that might be fed to the machine learning model; for a machine learning model that is designed to analyze voice recordings, the simulation space can be the space of all possible voice recordings having different volumes and/or loudness/pressure levels, different pitches, different tones, and/or otherwise different sound signatures that might be fed to the machine learning model). In various instances, the source data segment can be considered as representing merely one point within the simulation space (e.g., one particular chest X-ray image in the space of all possible chest X-rays images; one particular voice recording in the space of all possible voice recordings). Various embodiments of the subject innovation can automatically generate a plurality of deployable training data segments based on the source data segment, such that many varied points within the simulation space are now represented by the plurality of deployable training data segments (e.g., the source data segment can be copied, and the copies can be manipulated and/or modulated such that they have various different permutations/combinations of features and/or properties so as to more fully represent the diversity of the simulation span). Specifically, in various aspects, the simulation space can be parametrized by defining one or more modifiable parameters that span the simulation space. As explained thoroughly herein, non-limiting examples of such modifiable parameters can include data elements/features of interest and/or background data elements/features that are insertable into the annotated source data segment, modality-based data characteristics/properties of the source data segment that can be modulated, and/or mathematical transformations that can be applied to the source data segment. In various cases, the plurality of deployable training data segments can be generated by starting with the source data segment and by applying any suitable combinations and/or permutations of values and/or states to the modifiable parameters. In various instances, the result can be that the plurality of deployable training data segments broadly and/or widely sample the simulation space. In other words, the plurality of deployable training data segments can represent a very large sampling and/or proportion of the simulation space (e.g., the plurality of deployable training images can represent, capture, and/or approximate the diversity of values/states in the simulation space). Training the machine learning model on the plurality of deployable training data segments can result in improved performance/efficacy as compared to training the machine learning model on the source data segment alone.

For instance, consider the following exemplary parametrization hierarchy. First, a simulation space can be defined (e.g., it can be the domain of possible input data segments having different data signatures that can be received by the machine learning model in question). Next, broad augmentation subspaces can be defined within the simulation space, where an augmentation subspace contains one or more related, augmentable parameters. For instance, as explained herein, a first augmentation subspace can be a space of insertable data elements/features, and the one or more related, augmentable parameters within the space of insertable data elements/features can include types of insertable data elements/features (e.g., when the data involved are images, such types of insertable data elements/features can include images of breathing tubes, images of pacemakers, images of implants, images of fluid sacs, images of lung growths, images of stomach gas), localizations of the insertable data elements/features (e.g., different insertable images can be inserted into different image locations), orientations of the insertable data elements/features (e.g., different insertable images can be inserted upside down, backwards, sideways), dimensions/intensities of the insertable data elements/features (e.g., different insertable images can be inserted with different sizes/shapes/thicknesses), and/or so on. As another example, a second augmentation subspace can be a space of modifiable modality-based characteristics, where the one or more related, augmentable parameters within the space of modifiable modality-based characteristics include any suitable data segment properties that depend upon and/or that can be otherwise related to the device modality that generated and/or captured the source data segments in question (e.g., gamma/radiation level of an image, brightness level of an image, contrast level of an image, blur level of an image, noise level of an image, texture of an image, device artifacts in an image). As yet another example, a third augmentation subspace can be a space of mathematical transformations, where the one or more related, augmentable parameters within the space of mathematical transformations include any suitable operations that can be applied to the data segments in question (e.g., image rotations, image reflections, image pans, image tilts, image zooms, image distortions). In various aspects, each of the one or more related, augmentable parameters within each augmentation subspace can vary over a corresponding continuous parametric range of values and/or states. For example, the gamma/radiation level of an image can vary continuously from a minimum value to a maximum value. Similarly, the contrast level of an image can vary continuously from a minimum value to a maximum value. In some cases, however, an augmentation parameter can have a corresponding discrete range of values and/or states (e.g., a modality artifact parameter can include a state corresponding to no depicted artifacts, a state corresponding to a depicted lens glare, a state corresponding to a depicted lens scratch, a state corresponding to both a depicted lens glare and a depicted lens scratch, and/or so on). In various aspects, a parametric sampling of values/states from the continuous (and/or discrete) parametric range of each augmentable parameter can be taken (e.g., for a given data segment, an augmentable parameter can have any of a set of possible values/states, and a parametric sampling for that augmentable parameter can be any suitable subset of the set of possible values/states). For example, a gamma/radiation level of an image can continuously vary from a minimum value (e.g., 1 unit) to a maximum value (e.g., 1000 units), and the parametric sampling can include the minimum value, the maximum value, and any suitable, regular step sizes and/or increments between the minimum value and the maximum (e.g., the parametric sampling of gamma level values can go from 1 to 1000 in steps/increments of 0.1). In various aspects, a source data segment can be converted into a plurality of deployable training data segments by augmenting the source data segment according to any suitable combinations and/or permutations of such sampled parametric ranges of values/states (e.g., copies of the source data segment can be made, and different copies can be modified so as to have/exhibit different permutations/combinations of values/states from the sampled parametric ranges). Thus, the result can be that the plurality of deployable training data segments more adequately span and/or represent the feature/property diversity of the simulation space than does the source data segment alone, and so training the machine learning model on the plurality of deployable training data segments can yield better model performance as compared to conventional training techniques.

Figure 23:
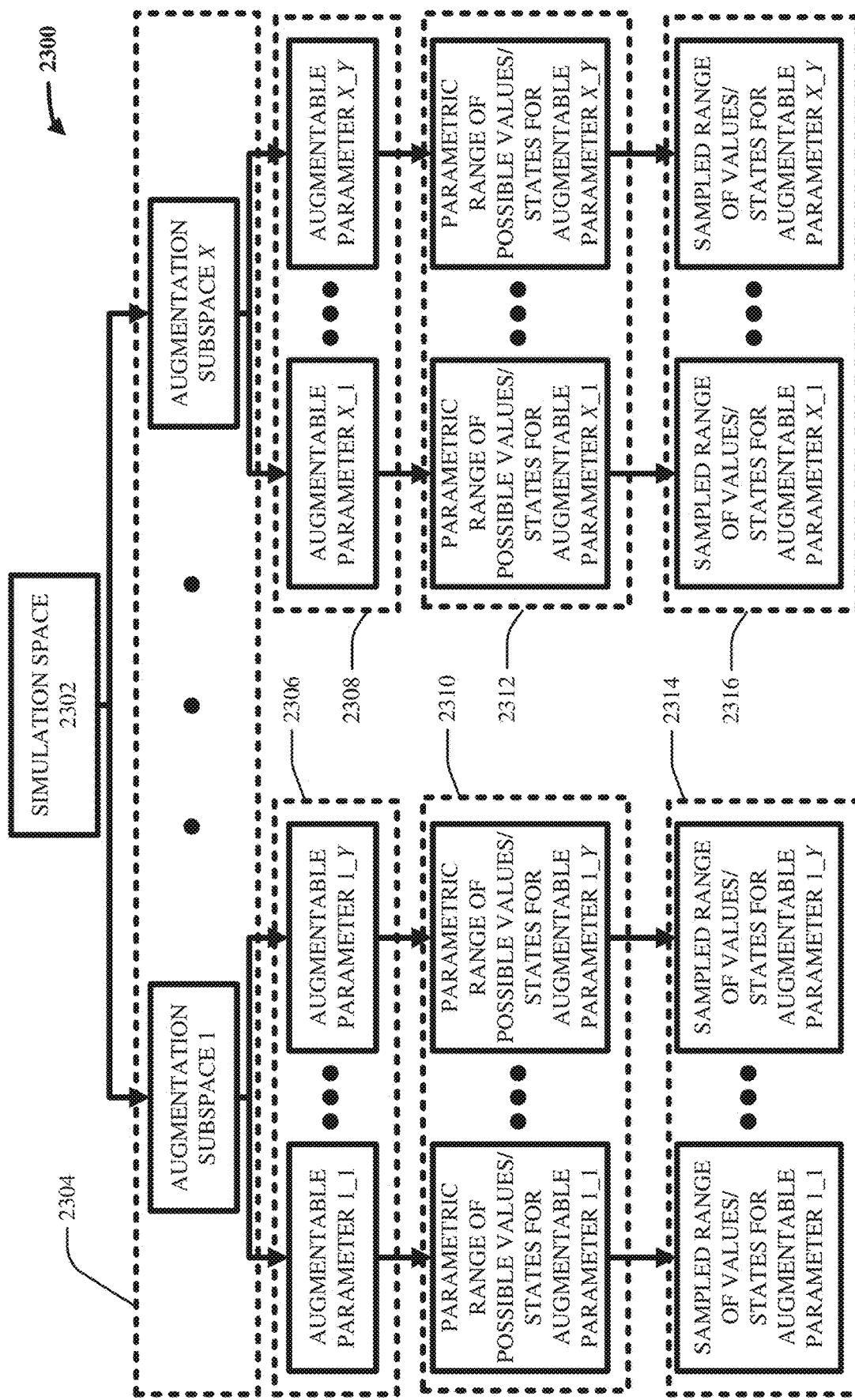
FIG. 23 illustrates a block diagram of an example, non-limiting augmentation space hierarchy that facilitates synthetic training data generation for improved machine learning model generalizability in accordance with one or more embodiments described herein.

FIG. 23 illustrates a block diagram of an example, non-limiting augmentation space hierarchy 2300 that can facilitate synthetic training data generation for improved machine learning model generalizability in accordance with one or more embodiments described herein. In various aspects, FIG. 23 can help to illustrate some of the aspects discussed above.

In various embodiments, it can be desired to train a machine learning model (e.g., 106). Accordingly, in various instances, a simulation space 2302 can be defined. In some cases, the simulation space 2302 can be the domain of all possible input data segments that can be received and/or analyzed by the machine learning model to be trained (e.g., if the machine learning model is configured to analyze brain CT scans, the simulation space 2302 can be the domain of all possible brain CT scans having different brain shapes, different anatomical features/properties, different disease states, different pixel values, and/or so on).

In various aspects, the simulation space 2302 can be decomposed into a set of augmentation subspaces 2304. In various aspects, as shown, X augmentation subspaces (e.g., augmentation subspace 1 to augmentation subspace X) can be defined for the simulation space 2302, for any suitable integer X. In various cases, each augmentation subspace can be considered as a space of related and augmentable parameters that collectively make up the simulation space 2302. As explained thoroughly above, non-limiting examples of such augmentation subspaces can include an element/feature subspace (e.g., a collection of augmentable parameters that relate to data elements/features that are insertable into data segments), a modality-based subspace (e.g., a collection of augmentable parameters that relate to settings of device modalities that capture/generate data segments and which can be modulated for data segments), and/or a data transformation subspace (e.g., a collection of augmentable parameters that relate to mathematical operations that can be applied to data segments).

In various aspects, each augmentation subspace can comprise a set of augmentable parameters. As shown, the augmentation subspace 1 can comprise the set of augmentable parameters 2306 (e.g., augmentable parameter 1_1 to augmentable parameter 1_Y, for any suitable integer Y). Similarly, the augmentation subspace X can comprise the set of augmentable parameters 2308 (e.g., augmentable parameter X_1 to augmentable parameter X_Y, for any suitable integer Y). Although FIG. 23 shows both the set of augmentable parameters 2306 and the set of augmentable parameters 2308 as having the same number of parameters (e.g., Y), this is exemplary and non-limiting. In various aspects, each set of augmentable parameters can have any suitable number of augmentable parameters (e.g., some sets having the same number of parameters, some sets having different numbers of parameters, and/or so on). As thoroughly explained above, non-limiting examples of such augmentable parameters can include the following: an element/feature augmentation subspace can include as augmentable parameters element/feature type, element/feature localization, element/feature dimensions, element/feature orientations, element/feature intensities, and/or so on; a modality-based subspace can include as augmentable parameters a brightness level, a contrast level, a noise/blur level, a resolution level, device artifacts, and/or so on; a data transformation subspace can include as augmentable parameters a reflection operation, a rotation operation, a panning/tilting/zooming operation, a distortion operation, and/or so on.

In various aspects, as shown, each augmentable parameter can have its own parametric range of possible values/states. For instance, the augmentable parameter 1_1 can have an associated parametric range of possible values/states for the augmentable parameter 1_1, the augmentable parameter 1_Y can have a parametric range of possible values/states for the augmentable parameter 1_Y, the augmentable parameter X_1 can have a parametric range of possible values/states for the augmentable parameter X_1, the augmentable parameter X_Y can have a parametric range of possible values/states for the augmentable parameter X_Y, and/or so on. As a non-limiting example, an augmentable parameter in an element/feature subspace can be type, and the corresponding parametric range of possible values/states can be all the possible types of elements/features which can be inserted into a data segment (e.g., images of pacemakers, images of implants, images of breathing tubes, images of electrocardiogram leads, images of lung growths, images of fluid sacs, images of stomach gas, and/or so on). As another non-limiting example, an augmentable parameter in an element/feature subspace can be localization, and the corresponding parametric range of possible values/states can be all the possible locations within a data segment where an element/feature can be inserted (e.g., top left of an image, bottom right of an image, middle of an image, and/or so on). As still another example, an augmentable parameter in an element/feature subspace can be orientation, and the corresponding parametric range of possible values/states can be all the possible orientations which an element/feature can have when inserted into a data segment (e.g., right side up, upside down, backwards, sideways, tilted, and/or so on). As another example, an augmentable parameter in a modality-based subspace can be brightness, and the corresponding parametric range of possible values/states can be all the possible brightness levels which a data segment can have (e.g., continuously ranging in magnitude from a minimum brightness to a maximum brightness). As yet another example, an augmentable parameter in a modality-based subspace can be contrast, and the corresponding parametric range of possible values/states can be all the possible contrast levels which a data segment can have (e.g., continuously ranging in magnitude from a minimum contrast to a maximum contrast). As still another example, an augmentable parameter in a modality-based subspace can be device artifacts, and the corresponding parametric range of possible values/states can be all the possible device artifacts which a data segment can have (e.g., lens glares of varying sizes/locations, lens scratches of varying sizes/locations, other lens occlusions like dust/dirt of varying sizes/locations, combinations of artifacts, no artifacts, and/or so on). As another example, an augmentable parameter in a data transformation subspace can be reflections, and the corresponding parametric range of possible values/states can be all the possible reflections that can be applied to a data segment (e.g., horizontal reflections, vertical reflections, reflections about any other suitable axis, and/or so on). As yet another example, an augmentable parameter in a data transformation subspace can be rotations, and the corresponding parametric range of possible values/states can be all the possible rotations that can be applied to a data segment (e.g., continuously ranging in magnitude from a minimum angular rotation to a maximum angular rotation). As still another example, an augmentable parameter in a data transformation subspace can be distortions, and the corresponding parametric range of possible values/states can be all the possible distortions that can be applied to a data segment (e.g., barrel distortions of varying magnitude, mustache distortions of varying magnitude, pincushion distortions of varying magnitude, combinations of distortions, no distortions, and/or so on).

In various aspects, the parametric range of possible values/states for the augmentable parameter 1_1 and the parametric range of possible values/states for the augmentable parameter 1_Y can be considered as a set of parametric ranges of possible values/states 2310, which set corresponds to the set of augmentable parameters 2306. In various instances, the set of parametric ranges of possible values/states 2310 can be considered as all the possible values/states that span the augmentation subspace 1. Similarly, the parametric range of possible values/states for the augmentable parameter X_1 and the parametric range of possible values/states for the augmentable parameter X_Y can be considered as a set of parametric ranges of possible values/states 2312, which set corresponds to the set of augmentable parameters 2308. In various instances, the set of parametric ranges of possible values/states 2312 can be considered as all the possible values/states that span the augmentation subspace X. Therefore, in some cases, the sets of parametric ranges of possible values/states 2310 and 2312 can collectively be considered as spanning the simulation space 2302.

In various embodiments, a sample can be taken of each parametric range of possible values/states. For instance, a sampled range of values/states for the augmentable parameter 1_1 can be taken from the parametric range of possible values/states for the augmentable parameter 1_1, a sampled range of values/states for the augmentable parameter 1_Y can be taken from the parametric range of possible values/states for the augmentable parameter 1_Y, a sampled range of values/states for the augmentable parameter X_1 can be taken from the parametric range of possible values/states for the augmentable parameter X_1, the sampled range of values/states for the augmentable parameter X_Y can be taken from the parametric range of possible values/states for the augmentable parameter X_Y, and/or so on. In various aspects, for a given parametric range of possible values/ states, a sampled range of values/states can be any suitable subset of the given parametric range of possible values/states. In various instances, such sampled ranges of values/states can be used to generate deployable training data segments as described herein. In other words, properties/characteristics of training data segments can be manipulated to take on any suitable combinations/permutations of the values/states represented in the sampled ranges of values/states. In various aspects, the sampled range of values/states for the augmentable parameter 1_1 and the sampled range of values/states for the augmentable parameter 1_Y can be considered as a set of sampled ranges of values/states 2314, which set corresponds to the set of parametric ranges of possible values/states 2310. Similarly, the sampled range of values/states for the augmentable parameter X_1 and the sampled range of values/states for the augmentable parameter X_Y can be considered as a set of sampled ranges of values/states 2316, which set corresponds to the set of parametric ranges of possible values/states 2312. In some cases, the sets of sampled ranges of values/states 2314 and 2316 can be collectively considered as an overall set and/or collection of values/states that represents and/or approximates the simulation space 2302 (e.g., that represents and/or approximates the diversity and/or variability of data features, data properties, and/or data characteristics within the simulation space 2302; in some cases, this can be a coarse and/or fine approximation of the diversity and/or variability of the simulation space 2302 depending upon the cardinality, resolution, and/or step sizes of the sampled ranges).

As explained thoroughly above, when deployable training data segments are synthetically generated based on the sets of sampled ranges of values/states 2314 and 2316, the deployable training data segments can more fully approximate and/or represent the variability and/or diversity of the simulation space 2302. Thus, training the machine learning model of interest on such deployable training data segments can result in improved model efficacy/performance as compared to traditional training techniques.

In various aspects, embodiments of the subject innovation can be considered as a robust and/or methodical technique for decomposing a simulation space (e.g., 2302) into augmentation subspaces (e.g., 2304), for decomposing the augmentation subspaces into augmentable parameters (e.g., 2306, 2308), for defining parametric ranges of possible values/states (e.g., 2310, 2312) for those augmentable parameters, for sampling (e.g., 2314, 2316) those parametric ranges of possible values/states, and for applying those sampled parametric ranges to training data segments such that those training data segments adequately span, represent, and/or capture the variability and/or diversity of the overall simulation space.

As explained above, in various aspects, embodiments of the subject innovation can update, change, and/or edit the parametrization of the simulation space 2302 (e.g., by defining and/or creating new and/or different augmentation subspaces in the set of augmentation subspaces 2304, by defining and/or creating new and/or different augmentable parameters for each augmentation subspace, by altering the parametric ranges of possible values/states for each augmentable parameter, and/or by taking different samples of the parametric ranges of possible values/states for each augmentable parameter).

Although various embodiments of the subject innovation are described herein as applying image/data augmentations in a specific order (e.g., first element insertion, then modality-based modulation, and finally geometric transformation), this is exemplary, non-limiting, and for ease of explanation. In various aspects, such image/data augmentations can be performed in any suitable order.

Machine learning model generalizability can be an important aspect of any artificial intelligence project. But generalizability can depend upon the availability and/or variety of annotated training data. Various embodiments of the subject innovation provide for systems and/or techniques that can synthetically generate varied training data based on a given piece of annotated training data. In various aspects, deterministic data augmentation can be applied as described herein to synthetically generate such varied training data. Specifically, element/feature insertion, modality-based modulation, and geometric transformations can be performed in any suitable order to synthetically generate voluminous and varied training data. As explained herein, training a machine learning model on such synthetically generated training data can result in significant performance/efficacy improvements. This performance/efficacy improvement can be achieved because the disclosed data augmentations can cause the synthetically generated training data to simulate and/or approximate real-world variability that the machine learning model is likely to encounter during operation.

In various embodiments, an image from a source dataset can be selected. In various aspects, any suitable permutation and/or combination of element/feature insertions, modality-based variations, and/or geometric transformations can be performed on the selected image to generate the deployable training images. In various aspects, any suitable augmentation policy/scheme can be implemented that controls how each image is augmented. In various aspects, each parameter of the augmentation policy can have its own range of values to be applied (e.g., rotation between 0 degrees and 360 degrees, gamma between 50 microwatts and 250 microwatts, and so on). In some cases, various augmentations can have an associated execution probability (e.g., meaning that the augmentation can be performed for fewer than all the images). In various aspects, any suitable augmentation policy/scheme can be implemented so as to improve/simulate real-world data variability. In some cases, different augmentation policies can be formulated based on data dimensionality (e.g., different policies for one-dimensional, two-dimensional, three-dimensional, and/or so on).

As shown above, various embodiments of the subject innovation are described with respect to the annotated source image 104. Specifically, various embodiments of the subject innovation can quickly and automatically generate the set of deployable training images 704 based on the annotated source image 104, where the set of deployable training images 704 can be used to facilitate supervised training of the machine learning model 106. However, in various other embodiments, the deployable training images 704 can be generated based on an unannotated source image (not shown in the figures). In such case, the deployable training images 704 could lack annotations/labels and could thus be used to facilitate unsupervised training and/or reinforcement learning of the machine learning model 106. In other words, those having ordinary skill in the art will appreciate that the herein teachings can be applied to an annotated source image as well as an unannotated source image.

Figure 24:
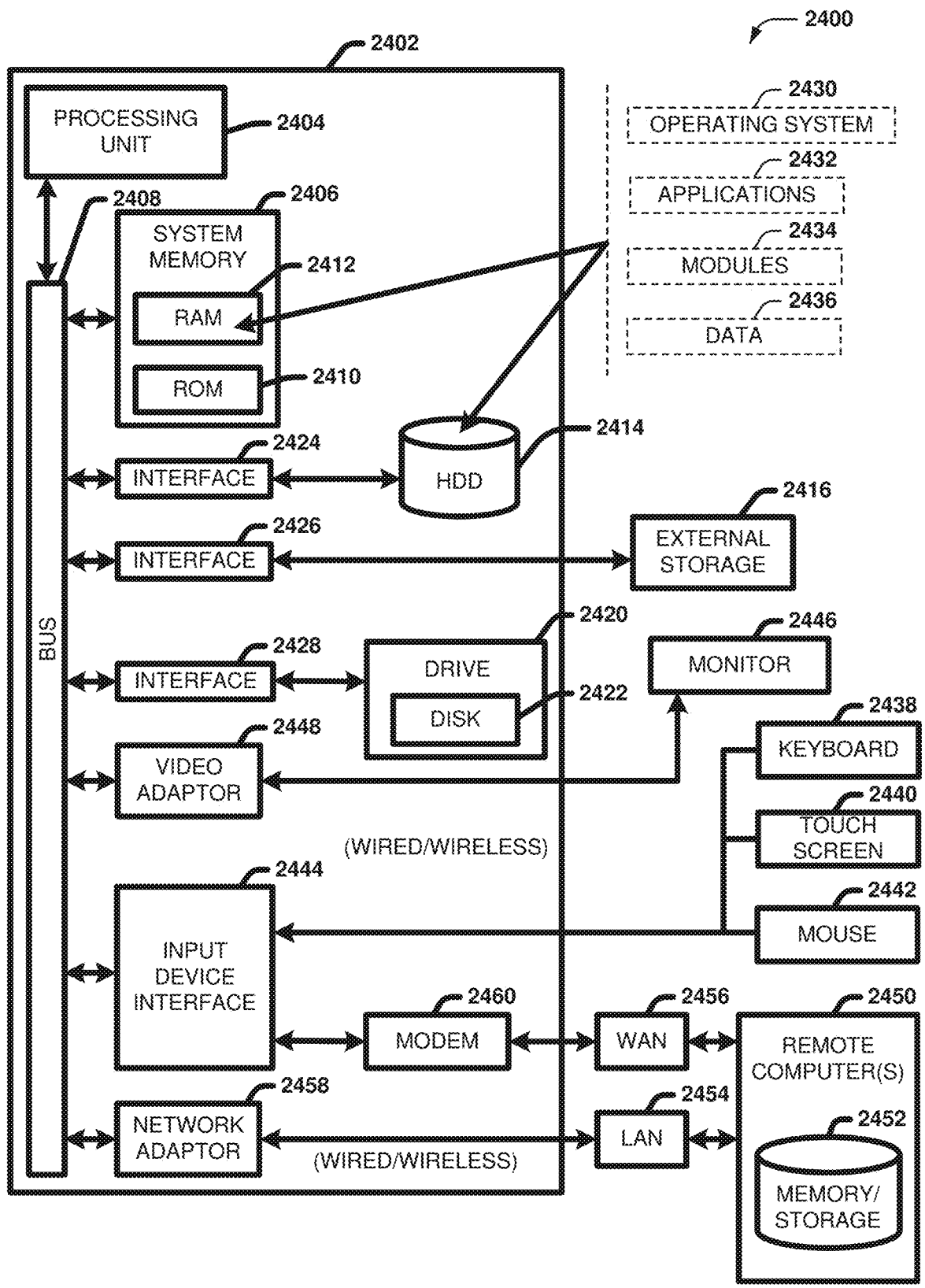
FIG. 24 illustrates a block diagram of an example, non-limiting operating environment in which one or more embodiments described herein can be facilitated.

In order to provide additional context for various embodiments described herein, FIG. 24 and the following discussion are intended to provide a brief, general description of a suitable computing environment 2400 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 24, the example environment 2400 for implementing various embodiments of the aspects described herein includes a computer 2402, the computer 2402 including a processing unit 2404, a system memory 2406 and a system bus 2408. The system bus 2408 couples system components including, but not limited to, the system memory 2406 to the processing unit 2404. The processing unit 2404 can be any of various commercially available processors. Dual microprocessors and other multi-processor architectures can also be employed as the processing unit 2404.

The system bus 2408 can be any of several types of bus structure that can further interconnect to a memory bus (with or without a memory controller), a peripheral bus, and a local bus using any of a variety of commercially available bus architectures. The system memory 2406 includes ROM 2410 and RAM 2412. A basic input/output system (BIOS) can be stored in a non-volatile memory such as ROM, erasable programmable read only memory (EPROM), EEPROM, which BIOS contains the basic routines that help to transfer information between elements within the computer 2402, such as during startup. The RAM 2412 can also include a high-speed RAM such as static RAM for caching data.

The computer 2402 further includes an internal hard disk drive (HDD) 2414 (e.g., EIDE, SATA), one or more external storage devices 2416 (e.g., a magnetic floppy disk drive (FDD) 2416, a memory stick or flash drive reader, a memory card reader, etc.) and a drive 2420, e.g., such as a solid state drive, an optical disk drive, which can read or write from a disk 2422, such as a CD-ROM disc, a DVD, a BD, etc. Alternatively, where a solid state drive is involved, disk 2422 would not be included, unless separate. While the internal HDD 2414 is illustrated as located within the computer 2402, the internal HDD 2414 can also be configured for external use in a suitable chassis (not shown). Additionally, while not shown in environment 2400, a solid state drive (SSD) could be used in addition to, or in place of, an HDD 2414. The HDD 2414, external storage device(s) 2416 and drive 2420 can be connected to the system bus 2408 by an HDD interface 2424, an external storage interface 2426 and a drive interface 2428, respectively. The interface 2424 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 2402, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 2412, including an operating system 2430, one or more application programs 2432, other program modules 2434 and program data 2436. All or portions of the operating system, applications, modules, and/or data can also be cached in the RAM 2412. The systems and methods described herein can be implemented utilizing various commercially available operating systems or combinations of operating systems.

Computer 2402 can optionally comprise emulation technologies. For example, a hypervisor (not shown) or other intermediary can emulate a hardware environment for operating system 2430, and the emulated hardware can optionally be different from the hardware illustrated in FIG. 24. In such an embodiment, operating system 2430 can comprise one virtual machine (VM) of multiple VMs hosted at computer 2402. Furthermore, operating system 2430 can provide runtime environments, such as the Java runtime environment or the .NET framework, for applications 2432. Runtime environments are consistent execution environments that allow applications 2432 to run on any operating system that includes the runtime environment. Similarly, operating system 2430 can support containers, and applications 2432 can be in the form of containers, which are lightweight, standalone, executable packages of software that include, e.g., code, runtime, system tools, system libraries and settings for an application.

Further, computer 2402 can be enable with a security module, such as a trusted processing module (TPM). For instance with a TPM, boot components hash next in time boot components, and wait for a match of results to secured values, before loading a next boot component. This process can take place at any layer in the code execution stack of computer 2402, e.g., applied at the application execution level or at the operating system (OS) kernel level, thereby enabling security at any level of code execution.

A user can enter commands and information into the computer 2402 through one or more wired/wireless input devices, e.g., a keyboard 2438, a touch screen 2440, and a pointing device, such as a mouse 2442. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 2404 through an input device interface 2444 that can be coupled to the system bus 2408, but can be connected by other interfaces, such as a parallel port, an IEEE 1394 serial port, a game port, a USB port, an IR interface, a BLUETOOTH® interface, etc.

A monitor 2446 or other type of display device can be also connected to the system bus 2408 via an interface, such as a video adapter 2448. In addition to the monitor 2446, a computer typically includes other peripheral output devices (not shown), such as speakers, printers, etc.

The computer 2402 can operate in a networked environment using logical connections via wired and/or wireless communications to one or more remote computers, such as a remote computer(s) 2450. The remote computer(s) 2450 can be a workstation, a server computer, a router, a personal computer, portable computer, microprocessor-based entertainment appliance, a peer device or other common network node, and typically includes many or all of the elements described relative to the computer 2402, although, for purposes of brevity, only a memory/storage device 2452 is illustrated. The logical connections depicted include wired/wireless connectivity to a local area network (LAN) 2454 and/or larger networks, e.g., a wide area network (WAN) 2456. Such LAN and WAN networking environments are commonplace in offices and companies, and facilitate enterprise-wide computer networks, such as intranets, all of which can connect to a global communications network, e.g., the Internet.

When used in a LAN networking environment, the computer 2402 can be connected to the local network 2454 through a wired and/or wireless communication network interface or adapter 2458. The adapter 2458 can facilitate wired or wireless communication to the LAN 2454, which can also include a wireless access point (AP) disposed thereon for communicating with the adapter 2458 in a wireless mode.

When used in a WAN networking environment, the computer 2402 can include a modem 2460 or can be connected to a communications server on the WAN 2456 via other means for establishing communications over the WAN 2456, such as by way of the Internet. The modem 2460, which can be internal or external and a wired or wireless device, can be connected to the system bus 2408 via the input device interface 2444. In a networked environment, program modules depicted relative to the computer 2402 or portions thereof, can be stored in the remote memory/storage device 2452. It will be appreciated that the network connections shown are example and other means of establishing a communications link between the computers can be used.

When used in either a LAN or WAN networking environment, the computer 2402 can access cloud storage systems or other network-based storage systems in addition to, or in place of, external storage devices 2416 as described above, such as but not limited to a network virtual machine providing one or more aspects of storage or processing of information. Generally, a connection between the computer 2402 and a cloud storage system can be established over a LAN 2454 or WAN 2456 e.g., by the adapter 2458 or modem 2460, respectively. Upon connecting the computer 2402 to an associated cloud storage system, the external storage interface 2426 can, with the aid of the adapter 2458 and/or modem 2460, manage storage provided by the cloud storage system as it would other types of external storage. For instance, the external storage interface 2426 can be configured to provide access to cloud storage sources as if those sources were physically connected to the computer 2402.

The computer 2402 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 25:
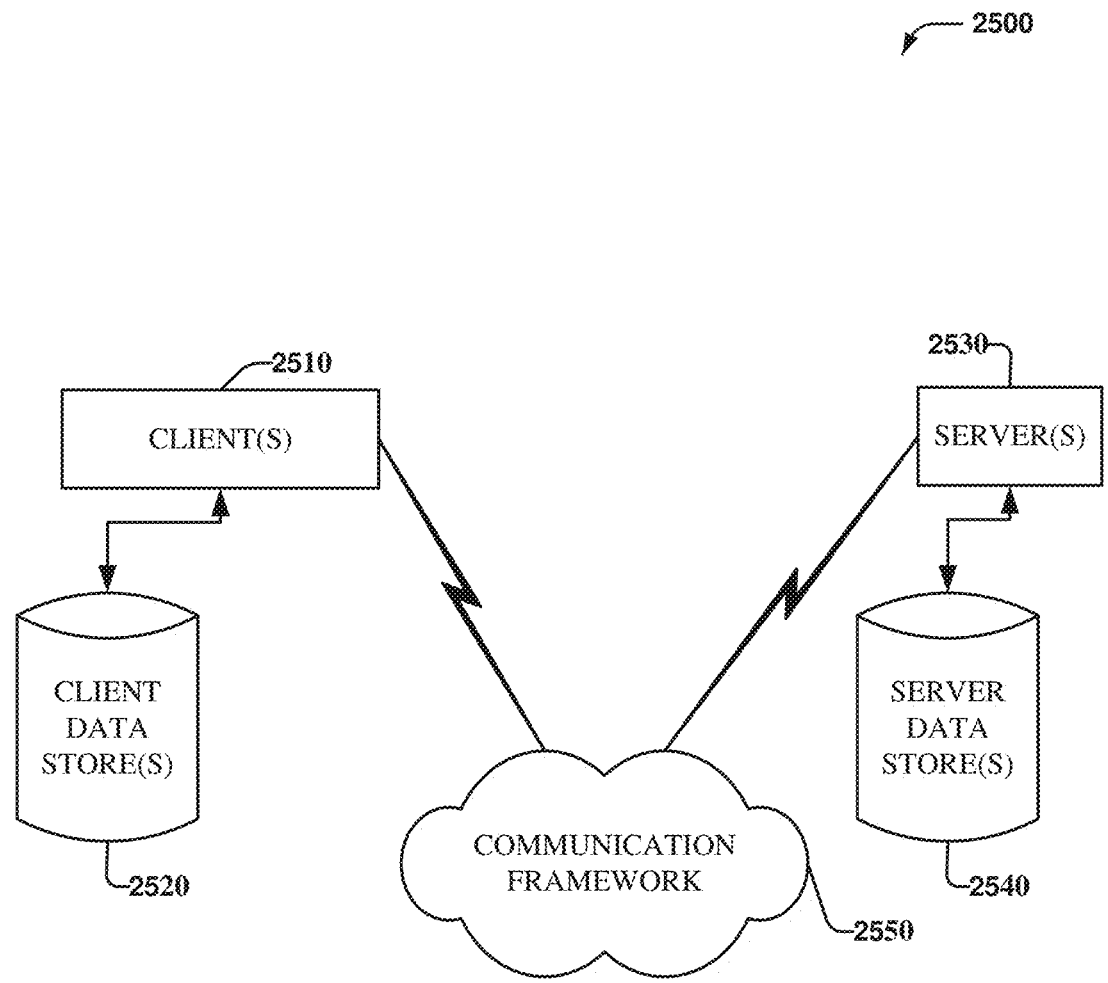
FIG. 25 illustrates an example networking environment operable to execute various implementations described herein.

FIG. 25 is a schematic block diagram of a sample computing environment 2500 with which the disclosed subject matter can interact. The sample computing environment 2500 includes one or more client(s) 2510. The client(s) 2510 can be hardware and/or software (e.g., threads, processes, computing devices). The sample computing environment

2500 also includes one or more server(s) 2530. The server(s) 2530 can also be hardware and/or software (e.g., threads, processes, computing devices). The servers 2530 can house threads to perform transformations by employing one or more embodiments as described herein, for example. One possible communication between a client 2510 and a server 2530 can be in the form of a data packet adapted to be transmitted between two or more computer processes. The sample computing environment 2500 includes a communication framework 2550 that can be employed to facilitate communications between the client(s) 2510 and the server(s) 2530. The client(s) 2510 are operably connected to one or more client data store(s) 2520 that can be employed to store information local to the client(s) 2510. Similarly, the server(s) 2530 are operably connected to one or more server data store(s) 2540 that can be employed to store information local to the servers 2530.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further aspects of various embodiments of the subject claimed innovation are provided in the subject matter that follows:

1. A system, comprising: a processor that executes computer-executable components stored in a memory, the computer-executable components comprising: an element augmentation component that generates a set of preliminary annotated training images based on an annotated source image, wherein a preliminary annotated training image is formed by inserting at least one element of interest or at least one background element into the annotated source image; a modality augmentation component that generates a set of intermediate annotated training images based on the set of preliminary annotated training images, wherein an intermediate annotated training image is formed by varying at least one modality-based characteristic of a preliminary annotated training image; and a geometry augmentation component that generates a set of deployable annotated training images based on the set of intermediate annotated training images, wherein a deployable annotated training image is formed by varying at least one geometric characteristic of an intermediate annotated training image.

2. The system of any preceding clause, wherein the computer-executable components further comprise: a training component that trains a machine learning model on the set of deployable annotated training images.

3. The system of any preceding clause, wherein the element augmentation component maintains an element catalog that lists a set of images of possible elements of interest and that lists a set of images of possible background elements that are insertable into the annotated source image, wherein the modality augmentation component maintains a list of modality-based characteristics that are modifiable in the preliminary training images, and wherein the geometry augmentation component maintains a list of geometric transformations that are appliable to the intermediate training images.

4. The system of any preceding clause, wherein the element augmentation component updates the element catalog by including within the element catalog a new image of an element of interest or a new image of a background element, wherein the modality augmentation component updates the list of modality-based characteristics by including within the list of modality-based characteristics new image properties that relate to device modality, and wherein the geometry augmentation component updates the list of geometric transformations by including within the list of geometric transformations new operations that are appliable to images.

5. The system of any preceding clause, wherein the at least one element of interest or the at least one background element is medical equipment or a biological symptom manifestation.

6. The system of any preceding clause, wherein the element augmentation component randomly localizes the at least one element of interest or the at least one background element in a range of biologically-possible locations within the annotated source image.

7. The system of any preceding clause, wherein the varying the at least one modality-based characteristic includes varying an image gamma level, varying an image blur level, varying an image brightness level, varying an image contrast level, varying an image noise level, varying an image texture, varying an image resolution, varying an image field of view, or applying a modality artifact.

8. The system of any preceding clause, wherein the varying the at least one geometric characteristic includes rotating about an image axis, reflecting about an image axis, image magnifying, image panning, image tilting, or image distorting.

9. A computer-implemented method, comprising: generating, by a device operatively coupled to a processor, a set of preliminary annotated training images based on an annotated source image, wherein a preliminary annotated training image is formed by inserting at least one element of interest or at least one background element into the annotated source image; generating, by the device, a set of intermediate annotated training images based on the set of preliminary annotated training images, wherein an intermediate annotated training image is formed by varying at least one modality-based characteristic of a preliminary annotated training image; and generating, by the device, a set of deployable annotated training images based on the set of intermediate annotated training images, wherein a deployable annotated training image is formed by varying at least one geometric characteristic of an intermediate annotated training image.

10. The computer-implemented method of any preceding clause, further comprising: training, by the device, a machine learning model on the set of deployable annotated training images.

11. The computer-implemented method of any preceding clause, further comprising: maintaining, by the device, an element catalog that lists a set of images of possible elements of interest and that lists a set of images of possible background elements that are insertable into the annotated source image; maintaining, by the device, a list of modality-based characteristics that are modifiable in the preliminary training images; and maintaining, by the device, a list of geometric transformations that are appliable to the intermediate training images.

12. The computer-implemented method of any preceding clause, further comprising: updating, by the device, the element catalog by including within the element catalog a new image of an element of interest or a new image of a background element; updating, by the device, the list of modality-based characteristics by including within the list of modality-based characteristics new image properties that relate to device modality; and updating, by the device, the list of geometric transformations by including within the list of geometric transformations new operations that are appliable to images.

13. The computer-implemented method of any preceding clause, wherein the at least one element of interest or the at least one background element is medical equipment or a biological symptom manifestation.

14. The computer-implemented method of any preceding clause, further comprising: randomly localizing, by the device, the at least one element of interest or the at least one background element in a range of biologically-possible locations within the annotated source image.

15. The computer-implemented method of any preceding clause, wherein the varying the at least one modality-based characteristic includes varying an image gamma level, varying an image blur level, varying an image brightness level, varying an image contrast level, varying an image noise level, varying an image texture, varying an image resolution, varying an image field of view, or applying a modality artifact.

16. The computer-implemented method of any preceding clause, wherein the varying the at least one geometric characteristic includes rotating about an image axis, reflecting about an image axis, image magnification, image panning, image tilting, or image distortion.

17. A computer program product for facilitating synthetic training data generation for improved machine learning generalizability, the computer program product comprising a computer readable memory having program instructions embodied therewith, the program instructions executable by a processor to cause the processor to: parametrize a simulation space of data segments by defining a set of augmentation subspaces, wherein each augmentation subspace comprises a corresponding set of augmentable parameters, and wherein each augmentable parameter has a corresponding parametric range of possible values or states; receive a source data segment; for each augmentable parameter, sample a parametric range of possible values or states corresponding to the augmentable parameter, thereby yielding a collection of sampled ranges of values or states that represents the simulation space; and generate a set of training data segments by applying the collection of sampled ranges of values or states to copies of the source data segment.

18. The computer program product of any preceding clause, wherein the program instructions are further executable to cause the processor to: train a machine learning model on the set of training data segments.

19. The computer program product of any preceding clause, wherein the program instructions are further executable to cause the processor to: update the parametrization of the simulation space by defining new augmentation subspaces.

20. The computer program product of any preceding claim, wherein the program instructions are further executable to cause the processor to: update the parametrization of the simulation space by defining new augmentable parameters within the set of augmentation subspaces.

What is claimed is:

1. A system, comprising:
a processor that executes computer-executable instructions stored in a memory, which causes the processor to:
access an annotated source image;
generate a set of preliminary annotated training images based on the annotated source image, wherein each preliminary annotated training image is formed by inserting a respective permutation of visual objects into the annotated source image, wherein such visual objects include medical equipment or biological symptoms;
generate a set of intermediate annotated training images based on the set of preliminary annotated training images, wherein each intermediate annotated training image is formed by applying a respective permutation of modality characteristic variations to a respective preliminary annotated training image, wherein such modality characteristic variations include changes to image properties that depend upon settings or parameters of a medical imaging device that captured or generated the annotated source image; and
generate a set of deployable annotated training images based on the set of intermediate annotated training images, wherein each deployable annotated training image is formed by applying a respective permutation of geometric variations to a respective intermediate annotated training image, wherein such geometric variations include spatial transformations of image pixel grids.

2. The system of claim 1, wherein execution of the computer-executable instructions further causes the processor to:
train a machine learning model on the set of deployable annotated training images.

3. The system of claim 1, wherein the system maintains an element catalog that lists a set of images of possible visual objects that are insertable into the annotated source image, wherein the system maintains a list of modality characteristics that are modifiable in the preliminary training images, and wherein the system maintains a list of geometric transformations that are appliable to the intermediate training images.

4. The system of claim 3, wherein the processor updates the element catalog by including within the element catalog a new image of a visual object, wherein the processor updates the list of modality characteristics by including within the list of modality characteristics new image properties that relate to device modality, and wherein the processor updates the list of geometric transformations by including within the list of geometric transformations new spatial operations that are appliable to images.

5. The system of claim 2, wherein the visual objects are objects of interest which the machine learning model is configured to detect.

6. The system of claim 1, wherein the processor randomly localizes the visual objects in a range of biologically-possible locations within the annotated source image.

7. The system of claim 1, wherein the applying a respective permutation of modality characteristic variations includes varying an image gamma level, varying an image blur level, varying an image brightness level, varying an image contrast level, varying an image noise level, varying an image texture, varying an image resolution, varying an image field of view, or applying a modality artifact.

8. The system of claim 1, wherein the applying a respective permutation of geometric variations includes rotating about an image axis, reflecting about an image axis, image magnifying, image panning, image tilting, or image distorting.

9. A computer-implemented method, comprising:
accessing, by a device operatively coupled to a processor, an annotated source image;
generating, by the device, a set of preliminary annotated training images based on the annotated source image, wherein each preliminary annotated training image is formed by inserting a respective permutation of visual objects into the annotated source image, wherein such visual objects include medical equipment or biological symptoms;
generating, by the device, a set of intermediate annotated training images based on the set of preliminary annotated training images, wherein each intermediate annotated training image is formed by applying a respective permutation of modality characteristic variations to a respective preliminary annotated training image, wherein such modality characteristic variations include changes to image properties that depend upon settings or parameters of a medical imaging device that captured or generated the annotated source image; and
generating, by the device, a set of deployable annotated training images based on the set of intermediate annotated training images, wherein each deployable annotated training image is formed by applying a respective permutation of geometric variations to a respective intermediate annotated training image, wherein such geometric variations include spatial transformations of image pixel grids.

10. The computer-implemented method of claim 9, further comprising:
training, by the device, a machine learning model on the set of deployable annotated training images.

11. The computer-implemented method of claim 9, further comprising:
maintaining, by the device, an element catalog that lists a set of images of possible visual objects that are insertable into the annotated source image;
maintaining, by the device, a list of modality characteristics that are modifiable in the preliminary training images; and
maintaining, by the device, a list of geometric transformations that are appliable to the intermediate training images.

12. The computer-implemented method of claim 11, further comprising:
updating, by the device, the element catalog by including within the element catalog a new image of a visual object;
updating, by the device, the list of modality characteristics by including within the list of modality characteristics new image properties that relate to device modality; and
updating, by the device, the list of geometric transformations by including within the list of geometric transformations new spatial operations that are appliable to images.

13. The computer-implemented method of claim 10, wherein the visual objects are objects of interest which the machine learning model is configured to detect.

14. The computer-implemented method of claim 9, further comprising:

randomly localizing, by the device, the visual objects in a range of biologically-possible locations within the annotated source image.

15. The computer-implemented method of claim 9, wherein the applying a respective permutation of modality characteristic variations includes varying an image gamma level, varying an image blur level, varying an image brightness level, varying an image contrast level, varying an image noise level, varying an image texture, varying an image resolution, varying an image field of view, or applying a modality artifact.

16. The computer-implemented method of claim 9, wherein the applying a respective permutation of geometric variations includes rotating about an image axis, reflecting about an image axis, image magnifying, image panning, image tilting, or image distorting.

17. A non-transitory computer program product for facilitating synthetic training data generation for improved machine learning generalizability, the non-transitory computer program product comprising a computer readable memory having program instructions embodied therewith, the program instructions executable by a processor to cause the processor to:
access an annotated source image;
generate a set of preliminary annotated training images based on the annotated source image, wherein each preliminary annotated training image is formed by inserting a respective permutation of visual objects into the annotated source image, wherein such visual objects include medical equipment or biological symptoms;
generate a set of intermediate annotated training images based on the set of preliminary annotated training images, wherein each intermediate annotated training image is formed by applying a respective permutation of modality characteristic variations to a respective preliminary annotated training image, wherein such modality characteristic variations include changes to image properties that depend upon settings or parameters of a medical imaging device that captured or generated the annotated source image; and
generate a set of deployable annotated training images based on the set of intermediate annotated training images, wherein each deployable annotated training image is formed by applying a respective permutation of geometric variations to a respective intermediate annotated training image, wherein such geometric variations include spatial transformations of image pixel grids.

18. The non-transitory computer program product of claim 17, wherein the program instructions are further executable to cause the processor to:
train a machine learning model on the set of deployable annotated training images.

19. The non-transitory computer program product of claim 17, wherein the program instructions are further executable to cause the processor to:
maintain an element catalog that lists a set of images of possible visual objects that are insertable into the annotated source image;
maintain a list of modality characteristics that are modifiable in the preliminary training images; and
maintain a list of geometric transformations that are appliable to the intermediate training images.

20. The non-transitory computer program product of claim 19, wherein the program instructions are further executable to cause the processor to:

update the element catalog by including within the element catalog a new image of a visual object;
update the list of modality characteristics by including within the list of modality characteristics new image properties that relate to device modality; and
update the list of geometric transformations by including within the list of geometric transformations new spatial operations that are appliable to images.

* * * * *